US011357568B2

(12) United States Patent
Panescu et al.

(10) Patent No.: US 11,357,568 B2
(45) Date of Patent: Jun. 14, 2022

(54) RADIOMETRIC TISSUE CONTACT AND TISSUE TYPE DETECTION

(71) Applicant: EPIX THERAPEUTICS, INC., Santa Clara, CA (US)

(72) Inventors: Dorin Panescu, San Jose, CA (US); Jessi E. Johnson, Santa Clara, CA (US); Josef Vincent Koblish, Santa Clara, CA (US); John F. McCarthy, Newbury, NH (US)

(73) Assignee: Epix Therapeutics, Inc., Santa Clara, CA (US)

( * ) Notice: Subject to any disclaimer, the term of this patent is extended or adjusted under 35 U.S.C. 154(b) by 424 days.

(21) Appl. No.: 15/527,924

(22) PCT Filed: Nov. 18, 2015

(86) PCT No.: PCT/US2015/061347
§ 371 (c)(1),
(2) Date: May 18, 2017

(87) PCT Pub. No.: WO2016/081602
PCT Pub. Date: May 26, 2016

(65) Prior Publication Data
US 2018/0310988 A1 Nov. 1, 2018

Related U.S. Application Data

(60) Provisional application No. 62/105,366, filed on Jan. 20, 2015, provisional application No. 62/087,678, (Continued)

(51) Int. Cl.
*A61B 18/14* (2006.01)
*A61B 18/12* (2006.01)
(Continued)

(52) U.S. Cl.
CPC ........ *A61B 18/1492* (2013.01); *A61B 5/0507* (2013.01); *A61B 5/6843* (2013.01);
(Continued)

(58) Field of Classification Search
None
See application file for complete search history.

(56) References Cited

U.S. PATENT DOCUMENTS 4,479,498 A * 10/1984 Toftness ............... A61B 5/05
600/407
4,557,272 A * 12/1985 Carr ...................... A61B 5/015
600/549

(Continued)

OTHER PUBLICATIONS

International Search Report dated Mar. 16, 2016 for corresponding International Application No. PCT/US2015/061347; International Filing Date Nov. 18, 2015, 4 pages.

*Primary Examiner* — Ronald Hupczey, Jr.
(74) *Attorney, Agent, or Firm* — Christopher & Weisberg, P.A.

(57) ABSTRACT

Radiometric systems may comprise a radiometer, an antenna and a processor communicatively coupled together. The processor may provide a contact-focused output based on filtering or other processing of a raw radiometric output signal. The contact-focused output may facilitate determination of whether contact has been achieved and/or assessment of contact. A miniaturized reflectometer may be configured to determine an amount of reflected power from the antenna. The processor may be configured to determine a reflection coefficient of the reflected power determined by the reflectometer and to identify tissue type based on the reflection coefficient. Systems and methods for facilitating deeper temperature measurements of a radiometer are described.

18 Claims, 14 Drawing Sheets

Related U.S. Application Data filed on Dec. 4, 2014, provisional application No. 62/081,697, filed on Nov. 19, 2014.

(51) Int. Cl.
  *A61B 5/00*      (2006.01)
  *A61B 5/0507*    (2021.01)
  *A61B 17/00*     (2006.01)
  *A61B 18/00*     (2006.01)
  *A61B 90/00*     (2016.01)

(52) U.S. Cl.
  CPC ........ *A61B 5/6852* (2013.01); *A61B 18/1206* (2013.01); *A61B 2017/00061* (2013.01); *A61B 2018/00357* (2013.01); *A61B 2018/00577* (2013.01); *A61B 2018/00648* (2013.01); *A61B 2018/00708* (2013.01); *A61B 2018/00738* (2013.01); *A61B 2018/00785* (2013.01); *A61B 2018/00791* (2013.01); *A61B 2018/00809* (2013.01); *A61B 2018/00904* (2013.01); *A61B 2090/065* (2016.02)

(56) References Cited

U.S. PATENT DOCUMENTS

| | | | |
|---|---|---|---|
| 5,344,435 A | 9/1994 | Turner et al. | |
| 5,974,343 A | 10/1999 | Brevard et al. | |
| 5,992,419 A * | 11/1999 | Sterzer | A61B 18/18 128/898 |
| 6,847,848 B2 * | 1/2005 | Sterzer | A61B 18/18 607/101 |
| 8,206,380 B2 * | 6/2012 | Lenihan | A61B 18/1492 606/33 |
| 8,731,684 B2 * | 5/2014 | Carr | A61B 18/18 607/101 |
| 9,277,961 B2 * | 3/2016 | Panescu | A61B 18/12 |
| 2007/0299488 A1 | 12/2007 | Carr | |
| 2008/0314894 A1 * | 12/2008 | Cronin | H05B 6/80 219/690 |
| 2009/0012417 A1 * | 1/2009 | Carr | A61B 5/4076 600/549 |
| 2011/0295247 A1 | 12/2011 | Schlesinger et al. | |
| 2012/0108988 A1 * | 5/2012 | Ludwin | A61B 18/1492 600/508 |
| 2013/0204240 A1 * | 8/2013 | McCarthy | A61B 5/015 606/41 |
| 2015/0094608 A1 * | 4/2015 | Allison | G01K 11/006 600/549 |

\* cited by examiner

RADIOMETRIC TISSUE CONTACT AND TISSUE TYPE DETECTION

RELATED APPLICATIONS

This application claims priority to U.S. Provisional Application No. 62/081,697 filed Nov. 19, 2014; to U.S. Provisional Application No. 62/087,678 filed Dec. 4, 2014; and to U.S. Provisional Application No. 62/105,366 filed Jan. 20, 2015, the entire contents of each of which are incorporated herein by reference in their entirety.

BACKGROUND

Tissue ablation may be used to treat a variety of clinical disorders. For example, tissue ablation may be used to treat cardiac arrhythmias by destroying (for example, at least partially or completely ablating, interrupting, inhibiting, terminating conduction of, otherwise affecting, etc.) aberrant pathways that would otherwise conduct abnormal electrical signals to the heart muscle. Several ablation techniques have been developed, including cryoablation, microwave ablation, radio frequency (RF) ablation, and high frequency ultrasound ablation. For cardiac applications, such techniques are typically performed by a clinician who introduces a catheter having an ablative tip to the endocardium via the venous vasculature, positions the ablative tip adjacent to what the clinician believes to be an appropriate region of the endocardium based on tactile feedback, mapping electrocardiogram (ECG) signals, anatomy, and/or fluoroscopic imaging, actuates flow of an irrigant to cool the surface of the selected region, and then actuates the ablative tip for a period of time and at a power believed sufficient to destroy tissue in the selected region.

Medical microwave radiometry utilizes temperature dependent microwave radiation from tissue to non-invasively monitor thermal ablation procedures. The radiation is received by an antenna and the antenna receiving pattern determines the volume of tissue that is being characterized by the radiometer. In general, the frequency of the radiometer system will determine the volume of tissue being measured, with lower frequencies tending to correspond to a larger volume due to a greater penetration depth (lower conductivity) in tissue.

SUMMARY

In accordance with one embodiment, a system for facilitating determination of quality of contact between an energy delivery member and tissue prior to and during energy delivery includes a processor configured to receive an output signal from a radiometer carried by an energy delivery member; and to determine a level of tissue contact between the energy delivery member and tissue based, at least in part, upon the variability of the output signal. The determination of the level of tissue contact may optionally be based, at least in part, on a moving average of the output signal (radiometric response) and/or a variability index determined by subtracting the moving average from the output signal (radiometric response). The processor may optionally be configured to cause an indicator (color and/or textual information) of the level of tissue contact to be displayed on a display. The embodiment of the system may optionally include a single radiometer. The embodiment of the system may include a single energy delivery member and not multiple energy delivery members.

In accordance with several embodiments, a system for facilitating determination of quality of contact between an energy delivery device and tissue prior to and during energy delivery comprises a radiometer configured to be coupled to a processor. In several embodiments, the processor is specifically configured to execute computer-readable instructions stored in a non-transitory computer readable medium to provide an output (for example, qualitative or quantitative assessment) indicative of tissue contact based on a radiometric response (for example, output signal) received from the radiometer. The processor may also be configured to determine a level of tissue contact between a distal tip of the energy delivery device and targeted tissue to be ablated or otherwise treated based, at least in part, upon said output. In some embodiments, the processor is further configured to cause an indicator of the level of tissue contact to be displayed on a display (for example, a generator display). The various functions may be performed by software modules executed by the processor and stored in memory. In some embodiments, the output is based, at least in part, on a moving average of the radiometric response (for example, a 5-point moving average). In one embodiment, the output comprises a variability index determined by subtracting the moving average from the raw radiometric output signal (for example, voltage signal). The output may be configured to be output on the display to provide user feedback regarding contact detection and assessment.

The indicator may comprise a color (for example, red for poor or weak contact, yellow for questionable or medium contact, and green for good or strong contact). In some embodiments, the indicator comprises textual or graphical information indicative of the level of tissue contact, or indicative of whether contact is achieved or not. For example, a checkmark may appear to indicate that contact has occurred or that the contact is excellent or very strong. The indicator may automatically cause an energy delivery module to enter an energy delivery mode or may signal to a user that it is safe to initiate delivery of energy to the targeted tissue. In some embodiments, the output comprises an audible indication of contact or level of contact.

In some embodiments, the level of tissue contact is determined based upon a comparison to at least one threshold. The at least one threshold may comprise contact vs. no-contact threshold or a piecewise linear threshold to indicate gradual contact (for example, poor=>medium=>good=>excellent). Each qualitative contact assessment category may be indicated by a different color or other indicator. In some embodiments, the amount of contact may be provided as a quantitative assessment (for example, a percentage of electrode surface area covered).

In some embodiments, the at least one threshold is configured to be automatically adjusted based on historical variability information data. The automatic adjustment may be based on an auto-scaling function. The level of tissue contact can be selected from one of: poor contact, medium contact, good contact, and excellent contact, wherein different levels of tissue contact are displayed using different colors. Any number of qualitative indicators may be used.

In some embodiments, the processor is configured to provide an output indicative of a level of cardiac tissue contact based on raw radiometer data received from the radiometer. In one embodiment, the output is based on filtering of the radiometric response with a moving average filter. In accordance with several embodiments, the output is not substantially affected by the type of cardiac or other tissue being contacted.

In some embodiments, the system comprises or consists essentially of a radiofrequency energy generator having a display. The display may be configured to display a user interface that is configured to receive user input and display output for the user to observe. The user interface may include a touchscreen interface. The system may comprise or consist essentially of an energy source or supply (for example, RF generator) comprising one or more energy delivery members or elements (for example, RF electrodes) configured to deliver energy (such as ablative RF energy) provided by the energy source or supply.

In some embodiments, the processor is configured to extract variability information from a signal received from the radiometer, determine a level of tissue contact between a distal tip of the energy delivery device and tissue to be ablated based, at least in part, upon the variability information, and/or cause an output indicative of the level of tissue contact to be displayed on the display of the energy source. In one embodiment, the variability information is based on a moving average of the signal received from the radiometer. The determination based upon extraction of variability information may provide increased confidence that contact has been achieved over determinations based on the raw radiometer output signal. In some embodiments, the output is not substantially affected by the type of tissue being contacted.

In accordance with several embodiments, a method of determining contact between an energy delivery device and tissue prior to and during energy delivery comprises receiving an output signal from a radiometer. The contact determination may be provided without delivering any ablative energy and prior to delivery of ablative energy. In one embodiment, the method comprises or consists essentially of extracting variability information from the output signal of the radiometer and causing an output indicative of the variability information to be displayed on a display. The method may also comprise determining a level of tissue contact based, at least in part, on the variability information. The variability information may comprise a variability index determined by subtracting a moving average (for example, a 5-point moving average) from the output signal (such as voltage signal) of the radiometer. In some embodiments, the output to be displayed comprises a color indicative of the level of tissue contact. The output may comprise textual or graphical information, alone or in combination, and/or in combination with color indication information. In some embodiments, the output does not include textual information and is purely visual or graphical.

In some embodiments, a method of determining contact between an energy delivery device and tissue prior to and during energy delivery comprises receiving raw signal data (for example, voltage or temperature data) from a radiometer and determining a level of contact from the raw signal data by filtering the raw signal data with a moving average filter and then subtracting the moving average filter output from the raw signal data. In one embodiment, the method comprises causing an output indicative of quality of contact to be presented on a display based on the determined level of contact. The output, or indication, may comprise a color indicative of the quality of tissue contact (for example, red, yellow or green). The indication may also or alternatively comprise textual or quantitative (for example, percentage of total electrode contact) assessments. In various embodiments, the contact indication is purely qualitative and/or purely graphical or visual (without text).

In some embodiments, a method of determining contact between an energy delivery device and tissue prior to and during energy delivery comprises receiving raw signal data from a radiometer indicative of an amount of tissue contact and providing an output indicative of a qualitative assessment of a level of tissue contact based on the received radiometer data. Providing an output indicative of a qualitative assessment of a level of tissue contact may comprise filtering the raw signal data to isolate variability information using one or more filters implemented in hardware and/or software. In one embodiment, the method comprises causing the output to be displayed on a display.

In accordance with several embodiments, a system for facilitating determination of quality of contact between an energy delivery member of a medical instrument and tissue during an energy delivery procedure comprises a processor configured to receive an output signal from a radiometer carried by the medical instrument, to determine whether a variability in the output signal is within a threshold range, and to generate an action signal to cause an action if the variability in the output signal is outside of the threshold range. The threshold range may be a predetermined range of expected variability. The variability determination may be performed by calculating a slope of at least a portion of the output signal from the radiometer. The variability determination may be continuously performed at a regular (for example, periodic) interval. In various embodiments, the interval is between 0.1 and 2 seconds (for example, between 0.1 and 0.5 seconds, between 0.5 seconds and 1 second, between 1 second and 2 seconds, between 1 second and 1.5 seconds, between 0.1 and 1 second, between 0.5 and 1.5 seconds, and overlapping ranges thereof). In some embodiments, the action may be a user alert (for example, an audible or visual warning). In some embodiments, the action may be automatic termination of energy delivery by the energy delivery member of the medical instrument. In other embodiments, the action comprises an adjustment to one or more parameters of the energy delivery.

In accordance with several embodiments, a method of monitoring contact between an energy delivery member of a medical instrument and target tissue being treated comprises receiving an output signal from a radiometer of the medical instrument while the energy delivery member is delivering energy, determining a variability of the output signal, identifying whether the variability is within a threshold range and generating an action configured to alter the energy delivery by the energy delivery member when the variability is identified as being outside the threshold range. In some embodiments, the action comprises a user alert, such as an audible warning or a visual warning that is output on a display. In some embodiments, the action comprises automatic termination of the energy delivery or adjusting one or more parameters of the energy delivery. Determining the variability may comprise calculating a slope of at least a portion of the output signal from the radiometer. This calculation of slope may occur at a periodic interval. In one embodiment, the periodic interval is between 0.1 and 2 seconds.

In accordance with several embodiments, a system for determining tissue type using a reflectometer includes a tissue heating device (for example, ablation catheter) and a processor. The tissue heating device may include an elongate body having a proximal end and a distal end. An antenna may be positioned at the distal end of the elongate body. In one embodiment, a radiofrequency electrode is positioned at the distal end of the elongate body adapted to contact tissue of a subject and to deliver radiofrequency energy sufficient to heat (for example, ablate) the tissue. In one embodiment, the tissue heating device includes a radiometer positioned at the distal end of the elongate body. The radiometer may be configured to determine temperature at a depth from a surface of the tissue. In several embodiments, the tissue is cardiac tissue; however, other tissue may also be treated (for example, tissue of other organs or vessel walls).

In one embodiment, the heating device includes a miniaturized reflectometer positioned at the distal end of the elongate body. The reflectometer may advantageously be configured to directly measure (for example, determine, calculate) an amount of reflected power received from the antenna. In some embodiments, the reflected power received from the antenna may be filtered by a band-stop filter to avoid frequencies in an operating bandwidth of the radiometer, thereby reducing the likelihood of interference with the operation of the radiometer. In some embodiments, the radiometer is switched to a reference mode while the reflectometer is switched to the antenna.

A processor, controller or other computing device(s) is configured to determine a reflection coefficient of the reflected power and to identify a type of tissue based on the determined reflection coefficient. The reflectometer may be used to determine both the magnitude and phase of the reflection coefficient. The reflection coefficient may be determined at an operating frequency within an operating band of the radiometer (for example, at an operating frequency of the radiometer, such as 4 GHz) or at multiple frequencies outside the operating band of the radiometer and then interpolated using averaging circuits, filters or methods (digital and/or analog).

In some embodiments, the processor is further configured to determine whether the distal end of the elongate body is in contact with a target tissue to be heated (for example, ablated) based on the determined tissue type. The determined tissue type may, for example, provide information regarding whether an ablation procedure at a target ablation site has been successful. The processor may also execute a code module or set of instructions to automatically adjust or calibrate temperature measurements obtained by the radiometer based, at least in part, on the reflection coefficient measured, calculated or otherwise determined by the reflectometer, thereby enhancing operation of the radiometer.

The type of tissue identified by the processor may be, for example, non-ablated normal tissue, infarct tissue, or ablated tissue. The identified tissue type may provide confirmation of a successful ablation or an indication that the ablation was not effective and additional ablation time is required. The tissue may be cardiac tissue or tissue of other organs or vessels. In some embodiments, the tissue type may be determined to be blood or a tissue wall to facilitate determination of contact prior to ablation.

In some embodiments, the processor is configured to provide an output indicative of the tissue type and/or an output indicative of contact with tissue. For example, the output can indicate that contact has occurred or can provide a qualitative assessment of the level of contact (for example, excellent, good, poor, no contact). In various embodiments, the output indicative of tissue type may comprise a live reading of the reflection coefficient magnitude plotted as a bar graph or a live reading of the magnitude and phase of the reflection coefficient plotted on a Smith chart or polar plot. The output may be displayed on a display in communication with the processor. For example, in one embodiment, the output is displayed on a display of an energy delivery module (for example, a generator).

In some implementations, the reflectometer is configured to determine reflection coefficients at multiple frequencies outside the operation bandwidth of the radiometer and the processor is configured to determine a reflection coefficient at an operating frequency of the radiometer based on interpolation using the determined reflection coefficients at said multiple frequencies. As one example, if the radiometer is designed to operate at a frequency of 4 GHz, the reflectometer may determine reflection coefficients at 3 GHz and 5 GHz and then estimate the reflection coefficient at 4 GHz through interpolation techniques (for example, using an averaging circuit). Two or more frequencies may be used (for example, 2, 3, 4 or more).

In accordance with one embodiment, a cardiac ablation catheter comprises or consists essentially of an elongate body having a proximal end and a distal end, an antenna positioned at the distal end of the elongate body, a radiofrequency electrode positioned at the distal end of the elongate body adapted to contact tissue of a subject and to deliver radiofrequency energy sufficient to ablate the tissue, a radiometer positioned at the distal end of the elongate body and a miniaturized reflectometer positioned at the distal end of the elongate body. The radiometer is configured to determine temperature at a depth from a surface of cardiac tissue and the reflectometer is configured to determine a reflection coefficient based on an amount of reflected power received from the antenna. In one embodiment, the radiometer is switched to a reference mode while the reflectometer is switched to the antenna. In one embodiment, the reflected power received from the antenna is filtered by a band-stop filter to avoid frequencies in an operating bandwidth of the radiometer.

In accordance with several embodiments, a system for determining tissue type using a reflectometer comprises a means for connecting (for example, an electrical, mechanical, or electromechanical interface or input/output port) to a tissue ablation device comprising an antenna, an ablation element configured to contact tissue of a subject and to deliver energy or fluid sufficient to ablate the tissue, a radiometer and a miniaturized reflectometer configured to determine an amount of reflected power received from the antenna. The system also comprises a processor configured to determine a reflection coefficient of the reflected power and to determine a tissue type based on the reflection coefficient. The reflected power received from the antenna may be filtered by a band-stop filter to avoid frequencies in an operating bandwidth of the radiometer. In one embodiment, the radiometer is switched to reference mode while the reflectometer is switched to the antenna.

In accordance with several embodiments, a method of determining tissue type using a reflectometer within a radiometric ablation catheter or other tissue treatment device includes receiving power from an antenna of the radiometric ablation catheter. In some implementations, an impedance matching circuit or network is positioned between the antenna of the radiometric ablation catheter and the reflectometer circuit. The radiometer, in normal operation, switches back and forth between a reference mode and a measurement mode for calibration purposes. Accordingly, in some implementations, a switch is provided to switch the power that is normally directed to the radiometer to instead be directed to the reflectometer for performing reflection coefficient measurements or calculations while the radiometer is switched to a reference load. The switching may be controlled by one or more clocks. The method may include measuring, calculating or determining a reflection coefficient of the power using the reflectometer. The reflectometer may measure both the magnitude and phase of the reflection coefficients. In some embodiments, the method includes determining a tissue type based on the calculated or measured reflection coefficient.

In accordance with several embodiments, the method includes determining whether the ablation catheter is in contact with a target tissue to be ablated based on the determined tissue type and/or confirming whether an ablation procedure has been successful (or proving other feedback related to a tissue treatment procedure) based on the determined tissue type. In some implementations, the method advantageously includes automatically adjusting temperature measurements obtained by the radiometer based on the calculated reflection coefficient, thereby enhancing operation of the radiometer.

The method may also include generating an output indicative of the tissue type and/or tissue contact. The output indicative of contact may indicate whether or not contact has occurred or may indicate a level or quality of contact. In some implementations, the method includes displaying the output on a display of an energy delivery module (for example, a radiofrequency generator). The method may include interpolating between the reflection coefficients determined at multiple frequencies to estimate a reflection coefficient at the operating frequency of the radiometer.

In accordance with several embodiments, a method of determining tissue type using a reflectometer within a radiometric ablation catheter comprises filtering a reflectometer signal with a band-stop filter to avoid frequencies in an operating bandwidth of the radiometer, calculating a reflection coefficient of the power using a reflectometer; and determining a tissue type based on the calculated reflection coefficient. The reflection coefficient may be calculated by a processor based on an amount of power received by the reflectometer (for example, from an antenna of the radiometric ablation catheter). The tissue type determination and filtering may also be performed by the processor or other computing device(s). In some embodiments, the method comprises determining whether the ablation catheter is in contact with a target tissue to be ablated and/or confirming whether an ablation procedure has been successful based, at least in part, on the determined tissue type.

In some embodiments, the method comprises automatically adjusting temperature measurements obtained by the radiometer based on the calculated reflection coefficient. In some embodiments, the method comprises generating an output indicative of the tissue type and/or contact. The output indicative of contact may comprise an indication that contact has occurred or an indication of a level or quality of contact. In some embodiments, the method comprises displaying the output on a display of an energy delivery module (for example, a generator). In some embodiments, calculating a reflection coefficient of the power using a reflectometer comprises determining a magnitude and a phase of the reflection coefficient.

In some embodiments, the reflectometer is configured to determine reflection coefficients with respect to a reference load by utilizing a Dicke switch concept in which the input of the reflectometer is switched between the antenna and a reference load—and the output signal is fed into a synchronous detector circuit.

In accordance with several embodiments, a medical instrument for facilitating deeper temperature measurements by a radiometer comprises utilizing a higher frequency for the radiometer circuitry than the frequency of the antenna, or conversely comprises utilizing an antenna that is configured to operate at a frequency that is lower than an operational frequency (e.g., center frequency) of the radiometer circuitry. In some embodiments, the medical instrument does not require changing the operational frequency of the radiometer or replacing the radiometer with a lower-frequency radiometer. The medical instrument may comprise or consist essentially of an antenna and a radiometer or radiometer circuitry. In some embodiments, the medical instrument comprises a transition network (e.g., matching circuit) positioned between the antenna and the radiometer and/or a frequency multiplier configured to (a) amplify an output signal from the antenna or transition network and (b) increase (e.g., multiply) a frequency of the output signal from the antenna or transition network to an operational frequency of the radiometer. In various embodiments, the medical instrument is a catheter configured to diagnose and/or treat tissue. As one example, the medical instrument is a radiometric cardiac ablation catheter configured for use in ablating endocardial tissue sufficient to treat cardiac arrhythmia or fibrillation.

In some embodiments, the antenna is configured to operate at a frequency that is a fraction (for example, one-fourth, one-third, one-half) of the operational frequency of the radiometer. The transition network may be configured to multiply (for example, double, triple or quadruple) the frequency of the output signal from the antenna. In some embodiments, the medical instrument further comprises an ablation member (for example, a radiofrequency electrode) configured to deliver ablative energy to tissue (for example, endocardial tissue). In one embodiment, the ablation member consists of a single member.

In some embodiments, the center frequency of the radiometer is 4 GHz, corresponding to an operational frequency band of 3.6 GHz to 4.4 GHz. For such a center frequency, the antenna may be designed or tuned to receive signals having a center frequency of about 2 GHz, 1.33 GHz or 1 GHz and the transition network is configured to double, triple or quadruple the frequency of the signals received by the antenna before feeding them to the radiometer. In one embodiment, the medical instrument comprises a switch configured to switch input to the radiometer between the antenna and a reference load. The frequency multiplier may comprise an amplification component and a separate frequency multiplication component or the two components may be provided as a single integral component. In one embodiment, the transition network (for example, frequency multiplier) comprises a single stage (e.g., transistor) with input and output matching networks configured to provide a simultaneous match for low-noise amplification and frequency multiplication. In some embodiments, the low noise amplification component serves as the first gain stage of the radiometer circuit. Thus, the multiplication/transition stage and radiometer may be part of the same radiometer circuit.

In accordance with several embodiments, a non-invasive method for characterizing tissue or performing measurements of tissue at an increased depth is provided. In some embodiments, the method comprises receiving microwave energy from a target region using an antenna designed to receive microwaves having a frequency that is lower than an operational frequency of a radiometer using an antenna, increasing the frequency of the received microwave energy up to the operational frequency of the radiometer and outputting signals having the increased frequency to the radiometer, thereby facilitating measurements using the radiometer at increased depths compared to depths obtainable using frequencies within an operational frequency band of the radiometer. In some embodiments, the method comprises receiving microwave energy from a target region using an antenna designed to receive microwaves having a given frequency using an antenna, increasing the frequency of the received microwave energy up to a higher frequency, and utilizing the higher frequency signals in the radiometer, thereby facilitating the use of more spatially compact, higher frequency radiometer circuit implementations, and thereby allowing for space constraints within miniature ablation catheters.

In some embodiments, the operational frequency of the antenna is a fraction (for example, one-fourth, one-third, one-half) of the operational frequency of the radiometer. The step of increasing the frequency between the antenna to the radiometer may comprise multiplying the frequency (for example, doubling, tripling or quadrupling the frequency). The antenna, frequency multiplier, and radiometer may be positioned along a distal end of a cardiac ablation catheter, which may be configured to characterize, diagnose, and/or treat tissue at a depth.

In some embodiments, the method comprises amplifying the received microwave energy and/or filtering out noise from the received microwave energy. The method may comprise comprising determining tissue temperatures at a depth based on the signals output to the radiometer. In some embodiments, the method comprises determining tissue characteristics (for example, tissue type) based on the determined tissue temperatures. The tissue characteristics may be used for contact sensing, lesion volume or gap assessments, or treatment confirmation purposes. In some embodiments, delivery of energy or fluid to target tissue may be initiated, continued, adjusted or terminated based on tissue characteristics or other feedback determined by the radiometer in real time or substantially in real time from the output signals of the frequency multiplier, amplifier or transition network. For example, if it is determined that tissue has been sufficiently ablated, delivery of ablative energy or fluid may be terminated. As another example, if a lesion gap is detected or if it is determined that the tissue has not been sufficiently ablated, delivery of ablative energy or fluid may be adjusted (change in position of distal tip, change in orientation of distal tip, duration of delivery, power increase or decrease, irrigation or cooling increase or decrease, etc.) and/or continued.

In accordance with several embodiments, a method of facilitating temperature measurements of a radiometric system at increased depth without altering an operational frequency of a radiometer is provided. The method may comprise receiving electromagnetic energy from tissue using an antenna designed to receive electromagnetic energy having a frequency that is less than an operational frequency of the radiometer, increasing the frequency of the electromagnetic energy received by the antenna to the operational frequency of the radiometer and outputting signals having the increased frequency to the radiometer, thereby facilitating measurements using the radiometer at increased depths compared to depths obtainable using frequencies within an operational frequency band of the radiometer. In accordance with one embodiment, a method of facilitating temperature measurements of a radiometric system at a given depth while increasing the operational frequency of a radiometer comprises receiving electromagnetic energy at a given frequency, multiplying the frequency of the received electromagnetic emissions up to a higher frequency, and utilizing a higher frequency radiometer, thereby allowing spatially compact, high frequency circuit techniques to be utilized in the implementation of the radiometer circuit.

In some embodiments, the frequency of the antenna is a fraction of the operational frequency of the radiometer. In some embodiments, increasing the frequency comprises multiplying the frequency (for example, doubling, tripling or quadrupling the frequency). The method may comprise determining tissue temperatures at a depth based on the signals output to the radiometer and determining tissue characteristics (such as tissue type) based on the determined tissue temperatures.

In accordance with one embodiment, a method of facilitating temperature measurements of a radiometric system at increased depth without altering an operational frequency of a radiometer comprises receiving microwave energy from tissue using an antenna designed to receive microwaves having a frequency that is a fraction of an operational frequency of the radiometer, multiplying the frequency of the received microwave emissions up to the operational frequency of the radiometer and outputting signals having the multiplied frequency to the radiometer, thereby facilitating measurements using the radiometer at increased depths compared to depths obtainable using frequencies within an operational frequency band of the radiometer. In accordance with one embodiment, a method of facilitating temperature measurements of a radiometric system at a given depth while increasing the operational frequency of a radiometer comprises receiving microwave energy at a given frequency, multiplying the frequency of the received microwave emissions up to a higher frequency, and utilizing a higher frequency radiometer, thereby allowing spatially compact, high frequency circuit techniques to be utilized in the implementation of the radiometer circuit.

The methods summarized above and set forth in further detail below describe certain actions taken by a practitioner; however, it should be understood that they can also include the instruction of those actions by another party. For example, actions such as "positioning a distal tip of a catheter in contact with targeted tissue" include "instructing the positioning a distal tip of a catheter in contact with targeted tissue." Further aspects of embodiments of the invention will be discussed in the following portions of the specification. With respect to the drawings, elements from one figure may be combined with elements from the other figures.

BRIEF DESCRIPTION OF THE DRAWINGS

Specific embodiments will be described with reference to the following drawings.

DETAILED DESCRIPTION

Figure 1:
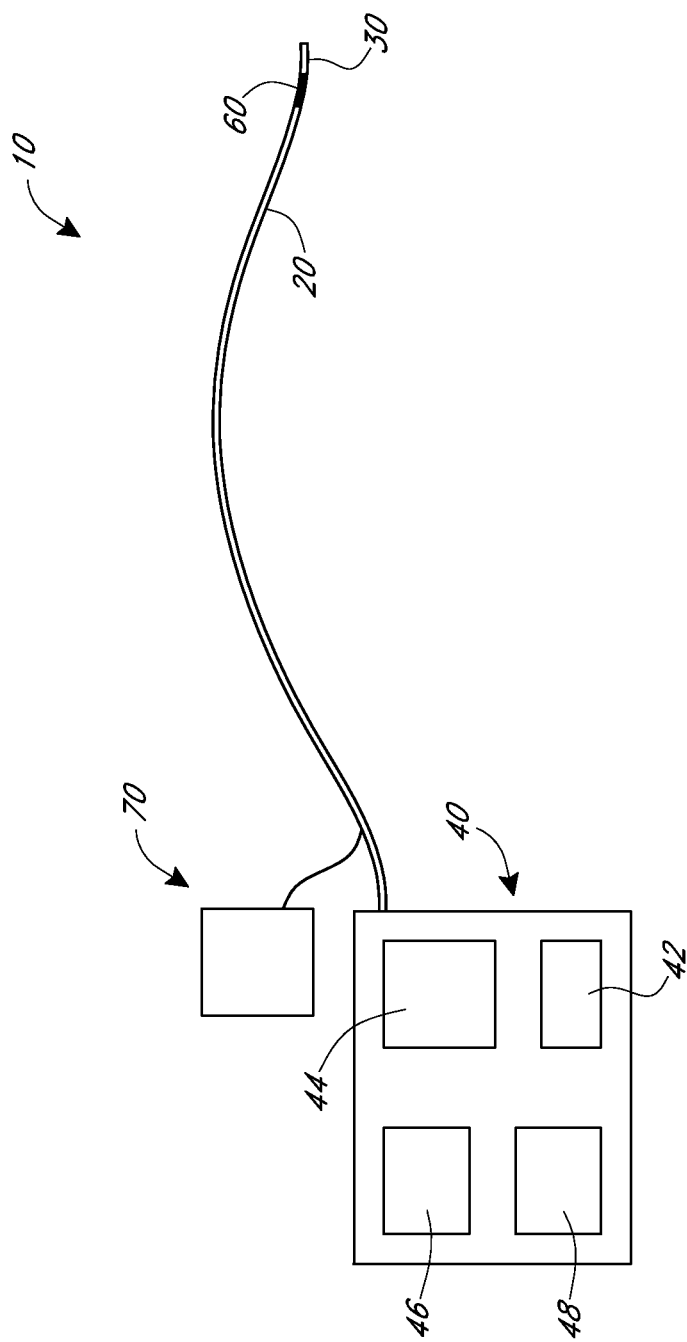
FIG. 1 schematically illustrates one embodiment of an energy delivery system 10 that is configured to selectively ablate or otherwise heat targeted tissue.

FIG. 1 schematically illustrates one embodiment of an energy delivery system 10 that is configured to selectively ablate or otherwise heat targeted tissue (for example, cardiac tissue, pulmonary vein, other vessels or organs, nerves, etc.). As shown, the system 10 can include a medical instrument 20 comprising one or more energy delivery members 30 (for example, radiofrequency electrodes, ultrasound transducers, microwave antennas) along a distal end of the medical instrument 20. The medical instrument can be sized, shaped and/or otherwise configured to be passed intraluminally (for example, intravascularly) through a subject being treated. In other embodiments, the medical instrument is not positioned intravascularly but is positioned extravascularly via laparoscopic or open surgical procedures. In various embodiments, the medical instrument 20 comprises a catheter, a shaft, a wire, and/or other elongate instrument. A radiometer 60 may be included at the distal end of the medical instrument 20, or along its elongate shaft or in its handle. The term "distal end" does not necessarily mean the distal terminus or distal end. Distal end could mean the distal terminus or a location spaced from the distal terminus but generally at a distal end portion of the medical instrument 20.

In some embodiments, the medical instrument 20 is operatively coupled to one or more devices or components. For example, as depicted in FIG. 1, the medical instrument 20 can be coupled to a delivery module 40 (such as an energy delivery module). According to some arrangements, the energy delivery module 40 includes an energy generation device 42 that is configured to selectively energize and/or otherwise activate the energy delivery member(s) 30 (for example, radiofrequency electrodes) located along the medical instrument 20. In some embodiments, for instance, the energy generation device 42 comprises a radiofrequency generator, an ultrasound energy source, a microwave energy source, a laser/light source, another type of energy source or generator, and the like, and combinations thereof. In other embodiments, energy generation device 42 is substituted with or use in addition to a source of fluid, such a cryogenic fluid or other fluid that modulates temperature. Likewise, the delivery module (for example, delivery module 40), as used herein, can also be a cryogenic device or other device that is configured for thermal modulation. Radiometer 60 may be configured to sense the temperature change of the targeted tissue in response to energy delivery or thermal modulation. The output of the radiometer 60 (for example, the radiometric voltage ($V_{rad}$)) may be passed back to the energy delivery module 40.

With continued reference to the schematic of FIG. 1, the energy delivery module 40 can include one or more input/output devices or components 44, such as, for example, a touchscreen device, a screen or other display, a controller (for example, button, knob, switch, dial, etc.), keypad, mouse, joystick, trackpad, microphone or other input device and/or the like. Such devices can permit a physician or other user to enter information into and/or receive information from the system 10. In some embodiments, the output device 44 can include a touchscreen or other display that provides tissue temperature information, contact information, other measurement information and/or other data or indicators that can be useful for regulating a particular treatment procedure.

According to some embodiments, the energy delivery module 40 includes a processor 46 (for example, a processing or control unit) that is configured to regulate one or more aspects of the treatment system 10. The processor 46 may include one or more conventional microprocessors that comprise hardware circuitry configured to read computer-executable instructions and to cause portions of the hardware circuitry to perform operations specifically defined by the circuitry. The output of radiometer 60 is processed by processor 46 so as to detect contact between delivery member 30 and tissue. The module 40 can also comprise a memory unit or other storage device 48 (for example, computer readable medium) that can be used to store operational parameters and/or other data related to the operation of the system 10. The storage device 48 may include random access memory ("RAM") for temporary storage of information and a read only memory ("ROM") for permanent storage of information, which may store some or all of the computer-executable instructions prior to being communicated to the processor 46 for execution, and/or a mass storage device, such as a hard drive, diskette, CD-ROM drive, a DVD-ROM drive, or optical media storage device, that may store the computer-executable instructions for relatively long periods of time, including, for example, when the computer system is turned off.

The modules and sub-modules of the system 10 may be connected using a standard based bus system. In different embodiments, the standard based bus system could be Peripheral Component Interconnect ("PCI"), Microchannel, Small Computer System Interface ("SCSI"), Industrial Standard Architecture ("ISA") and Extended ISA ("EISA") architectures, for example. In addition, the functionality provided for in the components and modules of computing system may be combined into fewer components and modules or further separated into additional components and modules.

The computing system is generally controlled and coordinated by operating system software, such as Windows 95, Windows 98, Windows NT, Windows 2000, Windows XP, Windows Vista, Windows 7, Windows 8, Unix, Linux, SunOS, Solaris, Maemeo, MeeGo, BlackBerry Tablet OS, Android, webOS, Sugar, Symbian OS, MAC OS X, or iOS or other operating systems. In other embodiments, the computing system may be controlled by a proprietary operating system. Conventional operating systems control and schedule computer processes for execution, perform memory management, provide file system, networking, I/O services, and provide a user interface, such as a graphical user interface ("GUI"), among other things.

The system 10 may also include one or more multimedia devices, such as speakers, video cards, graphics accelerators, and microphones, for example. A skilled artisan would appreciate that, in light of this disclosure, a system including all hardware components, such as the processor 46, I/O device(s) 44, storage device(s) 48 that are necessary to perform the operations illustrated in this application, is within the scope of the disclosure.

In some embodiments, the processor 46 is configured to automatically regulate the delivery of energy from the energy generation device 42 to the energy delivery member 30 of the medical instrument 20 based on one or more operational schemes. For example, energy provided to the energy delivery member 30 (and thus, the amount of heat transferred to or from the targeted tissue) can be regulated based on, among other things, the detected temperature of the tissue being treated.

According to some embodiments, the energy delivery system 10 can include one or more temperature detection devices, such as, for example, reference temperature devices (for example, thermocouples, thermistors, etc.), radiometers and/or the like.

With reference to FIG. 1, the energy delivery system 10 comprises (or is configured to be placed in fluid communication with) an irrigation fluid system 70. In some embodiments, as schematically illustrated in FIG. 1, such a fluid system 70 is at least partially separate from the energy delivery module 40 and/or other components of the system 10. However, in other embodiments, the irrigation fluid system 70 is incorporated, at least partially, into the energy delivery module 40. The irrigation fluid system 70 can include one or more pumps or other fluid transfer devices that are configured to selectively move fluid through one or more lumens or other passages of the medical instrument 20. Such fluid can be used to selectively cool (for example, transfer heat away from) the energy delivery member 30 during use.

The energy delivery system 10 may be used to selectively ablate or otherwise heat cardiac tissue (for example, myocardium, atrial tissue, ventricular tissue, valves, etc.), a bodily lumen (for example, vein, artery, airway, esophagus or other digestive tract lumen, urethra and/or other urinary tract vessels or lumens, other lumens, etc.), sphincters, other organs, tumors and/or other growths, nerve tissue and/or any other portion of the anatomy. The selective ablation and/or other heating of such anatomical locations can be used to treat one or more diseases or conditions, including, for example, atrial fibrillation, mitral valve regurgitation, other cardiac diseases, asthma, chronic obstructive pulmonary disease (COPD), other pulmonary or respiratory diseases, including benign or cancerous lung nodules, hypertension, heart failure, denervation, renal failure, obesity, diabetes, gastroesophageal reflux disease (GERD), other gastroenterological disorders, other nerve-related disease, tumors or other growths, pain and/or any other disease, condition or ailment.

Tissue Contact Detection

Figure 2:
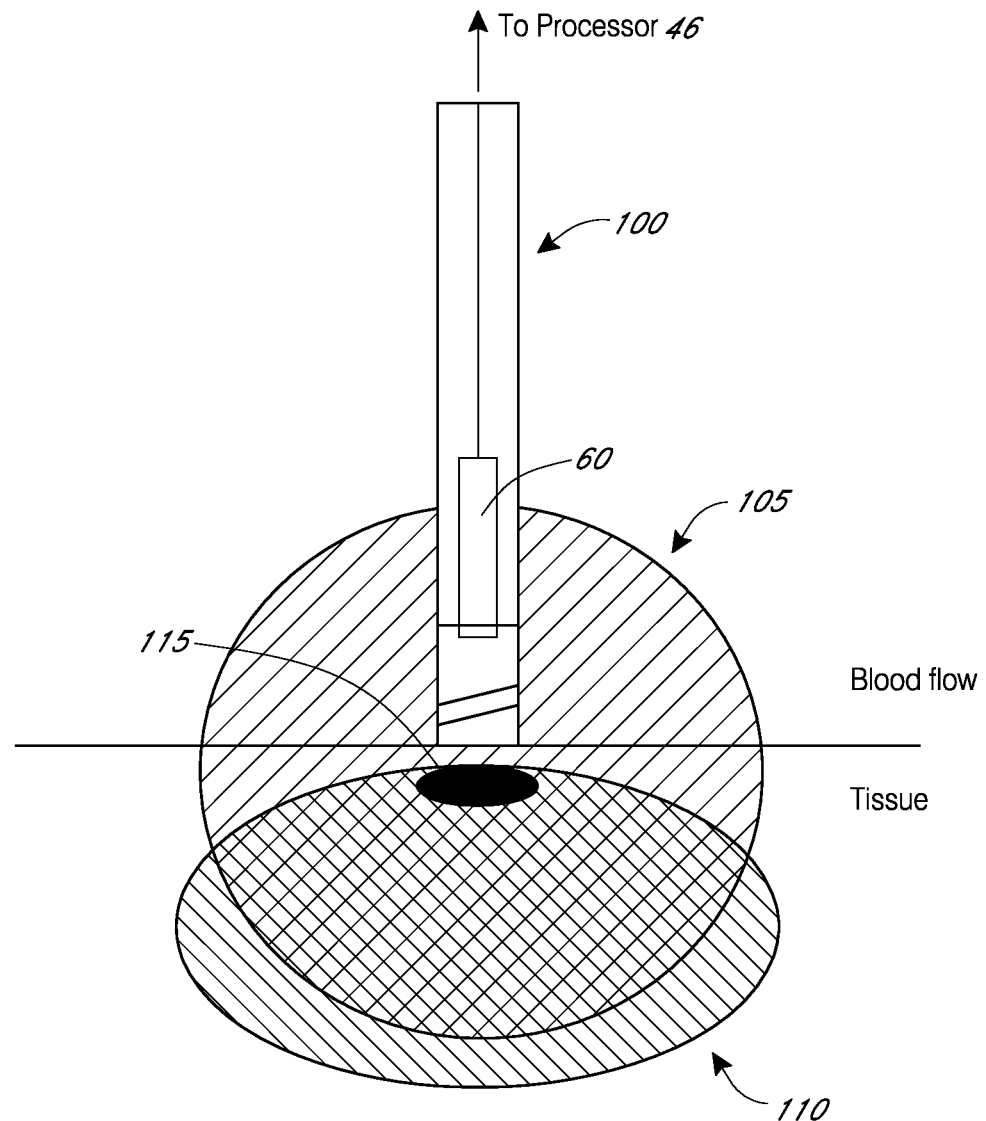
FIG. 2 schematically illustrates an embodiment of a distal tip of a radiofrequency ablation catheter having a microwave radiometer in contact with tissue, along with temperature and microwave zones pertaining thereto.

FIG. 2 illustrates an embodiment of a radiofrequency ablation catheter 100 in perpendicular contact with a tissue surface (for example, a cardiac wall or endocardial tissue). The radiofrequency ablation catheter 100 may represent the medical instrument 10 in FIG. 1. A distal tip of the ablation catheter 100 may comprise a member configured to function as both (1) an ablation electrode to deliver energy from the energy source (for example, radiofrequency generator) and (2) an antenna for the microwave radiometer 60. The antenna receives noise power from tissue and transmits the power to the radiometer 60. In some embodiments, the output of the radiometer 60, $V_{rad}$, is sent to the processor 46 to be processed for tissue contact detection and/or for tissue temperature monitoring. Tissue contact can be detected based on the difference in dielectric properties between blood and tissue. As shown in FIG. 2, the ablation catheter 100 may have a temperature/heating zone 110 and a microwave sensing zone 105. The radiometer 60 may measure temperature of a targeted tissue zone 115 at a depth from the tissue surface. Temperature is proportional to the noise power output according to the equation: Noise Power=kTb, where k is Boltzmann's constant, T is temperature in Kelvin and b is bandwidth in Hz.

Successful formation of ablation lesions is facilitated by achieving good contact between the ablation member (for example, radiofrequency electrode) and targeted tissue (for example, endocardial tissue). Several embodiments of the invention are particularly advantageous because they include one, several or all of the following benefits: (i) facilitate identification of an amount or level of contact (quality of contact) between the energy delivery member and targeted tissue prior to and/or during delivery of energy and does not include or require delivery of ablative energy; (ii) visual feedback indicative of quality of contact that is user-friendly and easy to understand; (iii) shorter procedure times due to increased efficiency; (iv) reduction in likelihood of undesired damage to tissue not intended to be ablated or otherwise treated; (v) increases accuracy of contact sensing and determination functionality by averaging the output to remove outliers that may result in false positives or erroneous readings; (vi) more useful information regarding contact by providing more than a binary "contact or no contact" determination; (vii) increase in likelihood of success of treatment; and/or (viii) not requiring additional sensors specifically dedicated for contact monitoring. Current approaches use dedicated sensors to measure contact force. Such dedicated sensors increase the cost of the catheter and may affect its ultimate performance. In accordance with several embodiments, the systems described herein use the same sensor (the radiometer) for tissue contact monitoring and for tissue temperature monitoring, thereby decreasing costs and reducing the likelihood of effects on system performance.

Figure 3:
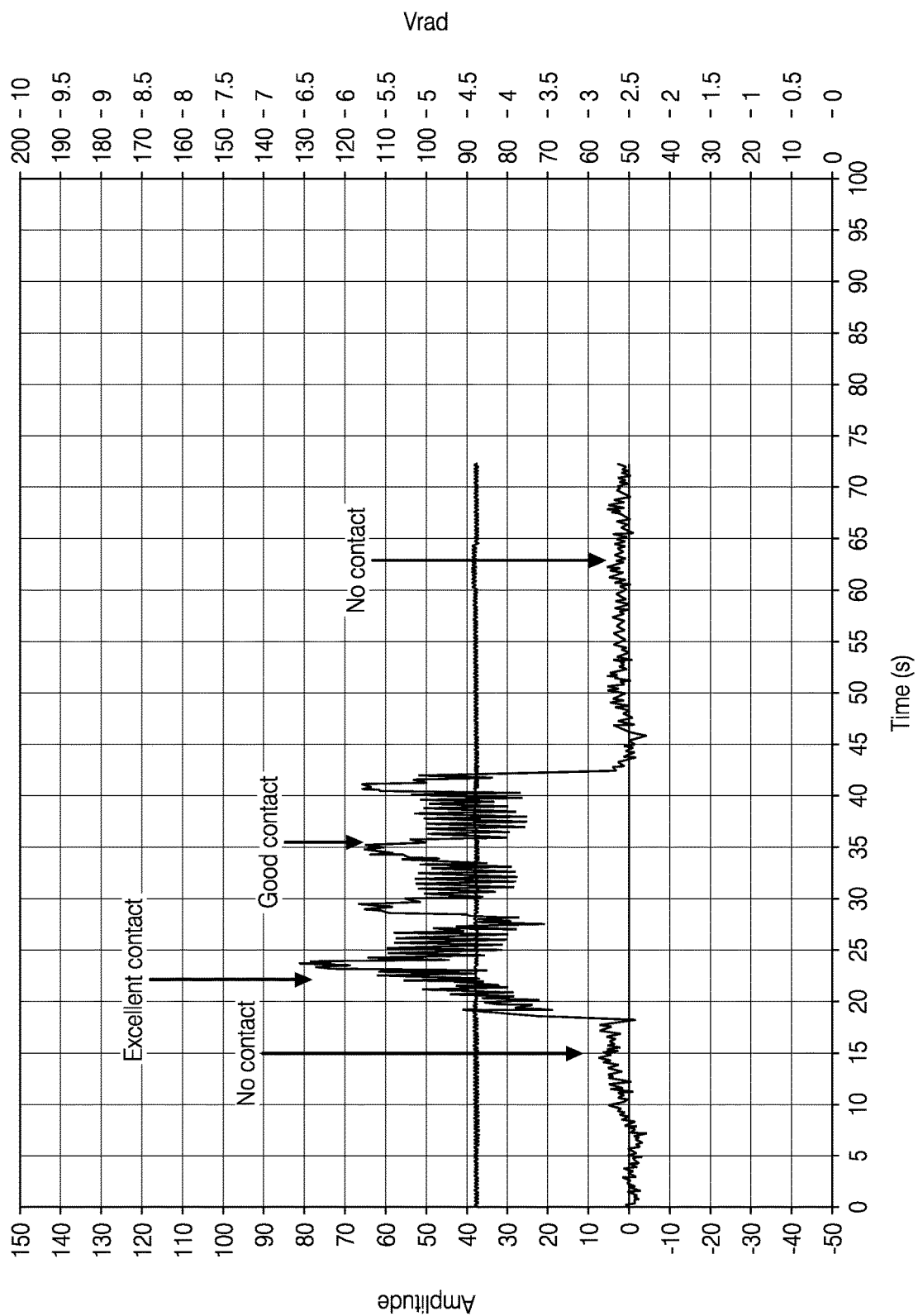
FIG. 3 is a plot illustrating an embodiment of an output of the microwave radiometer as an electrode approaches, contacts, and then separates from a tissue surface within a right atrium of a subject, with the level of contact identified at various time instances.

FIG. 3 is a graph illustrating raw output data, $V_{rad}$, of the microwave radiometer 60 as an electrode approaches, contacts, and then separates from a tissue surface within a right atrium of a subject. The graph illustrates a change in amplitude and a change in a voltage reading of the radiometer over time. According to some embodiments, the graph illustrates instances of no contact (when the amplitude is approximately zero), an instance of excellent contact and an instance of good contact. As can be seen in the graph of FIG. 3, there is an abrupt change in amplitude or voltage at the point of contact initiation. An abrupt change may be defined to be a change that is above a threshold or a change of a certain magnitude or scaling factor. However, in the depicted embodiment, there is also significant variation in the amplitude or voltage while the electrode is in contact with the tissue. In some embodiments, significant response can be noticed as the tissue contact increases to the "excellent" indication. In some embodiments, the contact signal level drops as tissue contact moves from "excellent" to "good." Details regarding determination and provision of indications of qualitative assessment of level or amount of contact based on radiometric response will be further addressed below.

Figure 4:
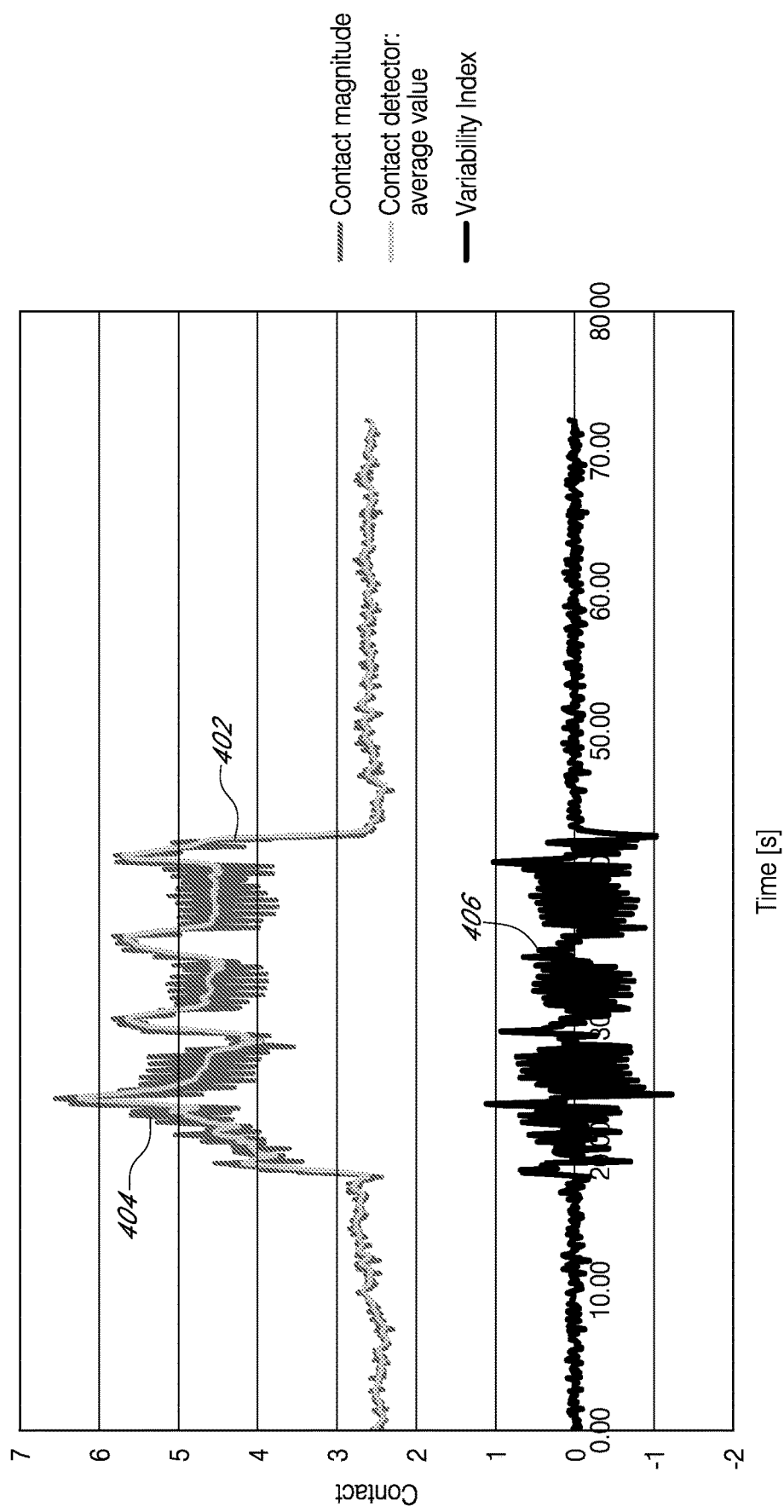
FIG. 4 shows an example of how the raw radiometer output shown in FIG. 3 can be processed to facilitate indication of contact, or an amount of contact.

In accordance with several embodiments, processing of the raw radiometer output can extract or isolate more relevant (and/or more reliable) contact information from the raw radiometer output to facilitate generation of indicators for a qualitative assessment of contact (for example, whether contact has been achieved or an amount of contact or level of contact). FIG. 4 shows an example of how the raw radiometer output shown in FIG. 3 can be processed to facilitate indication of contact, or an amount of contact. The line 402 in the graph of FIG. 4 represents a moving average of the raw radiometer output (indicated by the line 404). In the illustrated embodiment, the moving average comprises a five-point moving average; however, other types of moving averages or mean determinations may be used.

The line 406 at the bottom of the graph represents a variability index (VI) computed by subtracting the moving average (for example, 5-point moving average) from the raw radiometer output signal. The variability index would be generally flat before contact, with minor fluctuation due to variability (which may be patient-specific or dependent on location). A significant increase in amplitude of the variability index signal may be noted as contact to tissue is achieved. The significant increase in the variability index signal may provide increased confidence that contact has been achieved over the raw radiometer output signal. In some embodiments, the amount of response may be dependent on the amount of tissue contact. In accordance with several embodiments, the variability index may be computed according to the following equation:

$$VI(n) = V_{rad}(n) - \text{Mov\_avg\_}V_{rad}(n),$$

where $V_{rad}(n)$ is the output voltage of the radiometer and $\text{Mov\_avg\_}V_{rad}(n)$ represents the output of the moving average filter at time n. Accordingly, for a 5-point moving average filter, the moving average would be computed as follows:

$$\text{Mov\_avg\_}V_{rad}(n) = \frac{1}{5} * (V_{rad}(n-4) + V_{rad}(n-3) + V_{rad}(n-2) + V_{rad}(n-1) + V_{rad}(n))$$

The processing may comprise analog and/or digital signal processing techniques. In some embodiments, analog or digital amplifiers and/or filters may be used in the processing. The processing may be performed using software, hardware, or a combination of both. In some embodiments, the processing unit samples the signal $V_{rad}$ and produces samples $V_{rad}(n)$. The hardware, software or combination of hardware and software then computes the output $\text{Mov\_avg\_}V_{rad}(n)$, as shown above. The above example implements 5-point moving average assuming a 0.1 second sampling period. Thus, the length of the moving window is 0.5 seconds. Depending on the characteristics of the signal, a longer or shorter duration window length may be used.

Figure 5A:
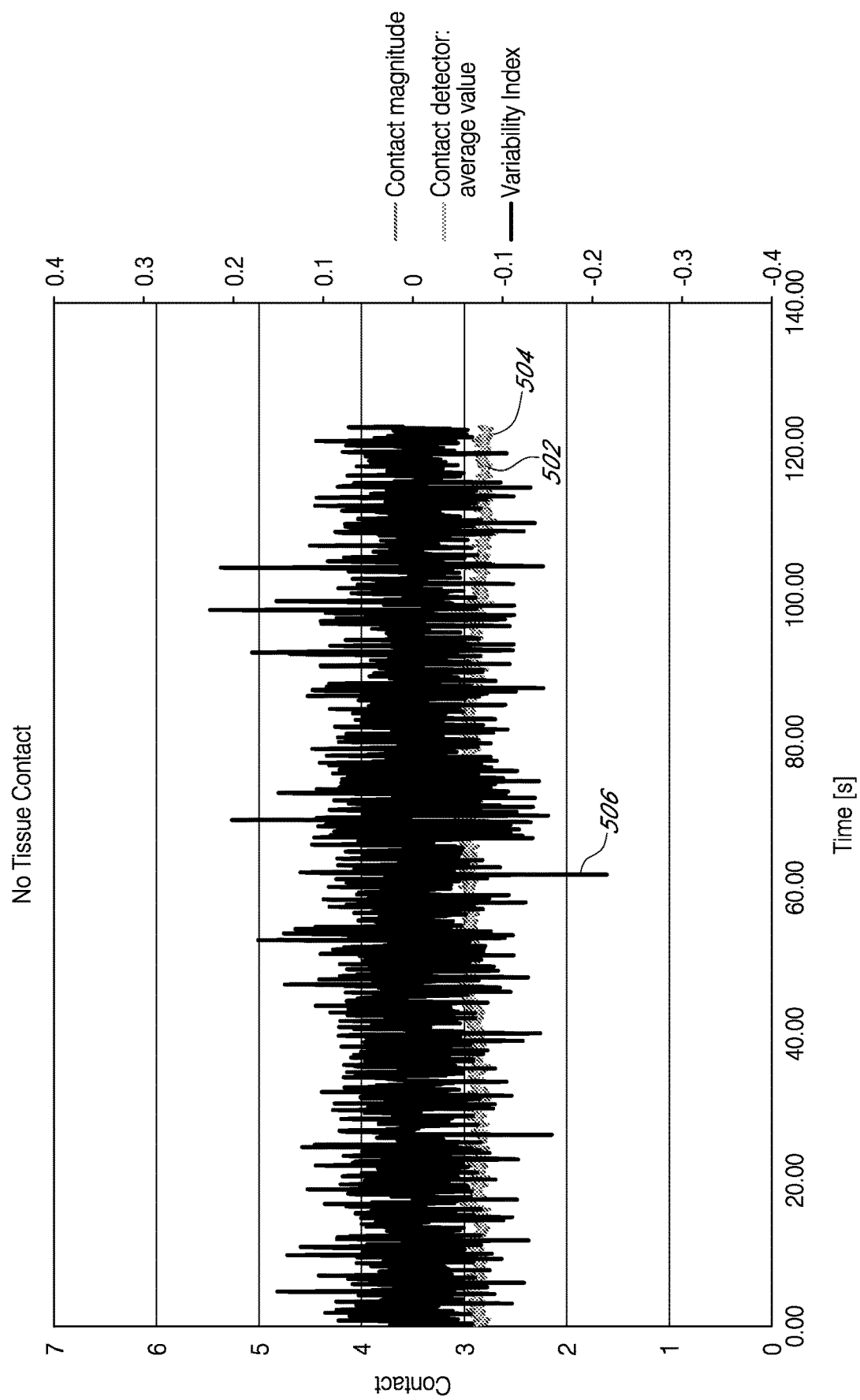
FIGS. 5A and 5B illustrate embodiments of similar processing techniques as shown in FIG. 4 for assessing contact in a left ventricle.
Figure 5B:
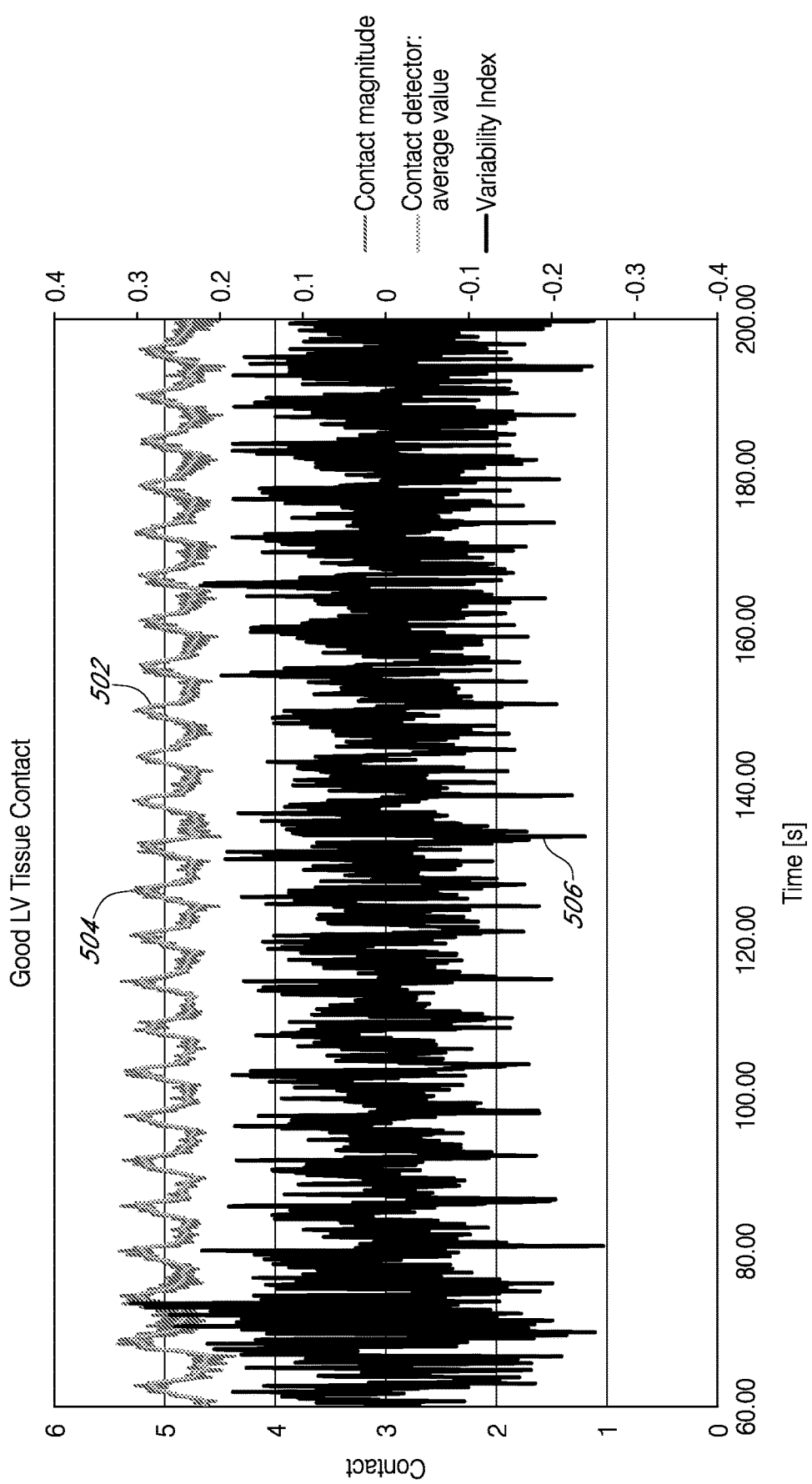

FIGS. 5A and 5B illustrate similar processing of a radiometer output signal as shown in FIG. 4 for assessing contact in a left ventricle. FIG. 5A illustrates a time when the electrode is not in contact with the left ventricle tissue and FIG. 5B illustrates a time when the electrode is in contact with the left ventricle tissue. Again, the lines 502 represent the moving average filter output signals, the lines 504 represent the raw radiometer output signals and the lines 506 represent the variability index output signals.

Figure 6:
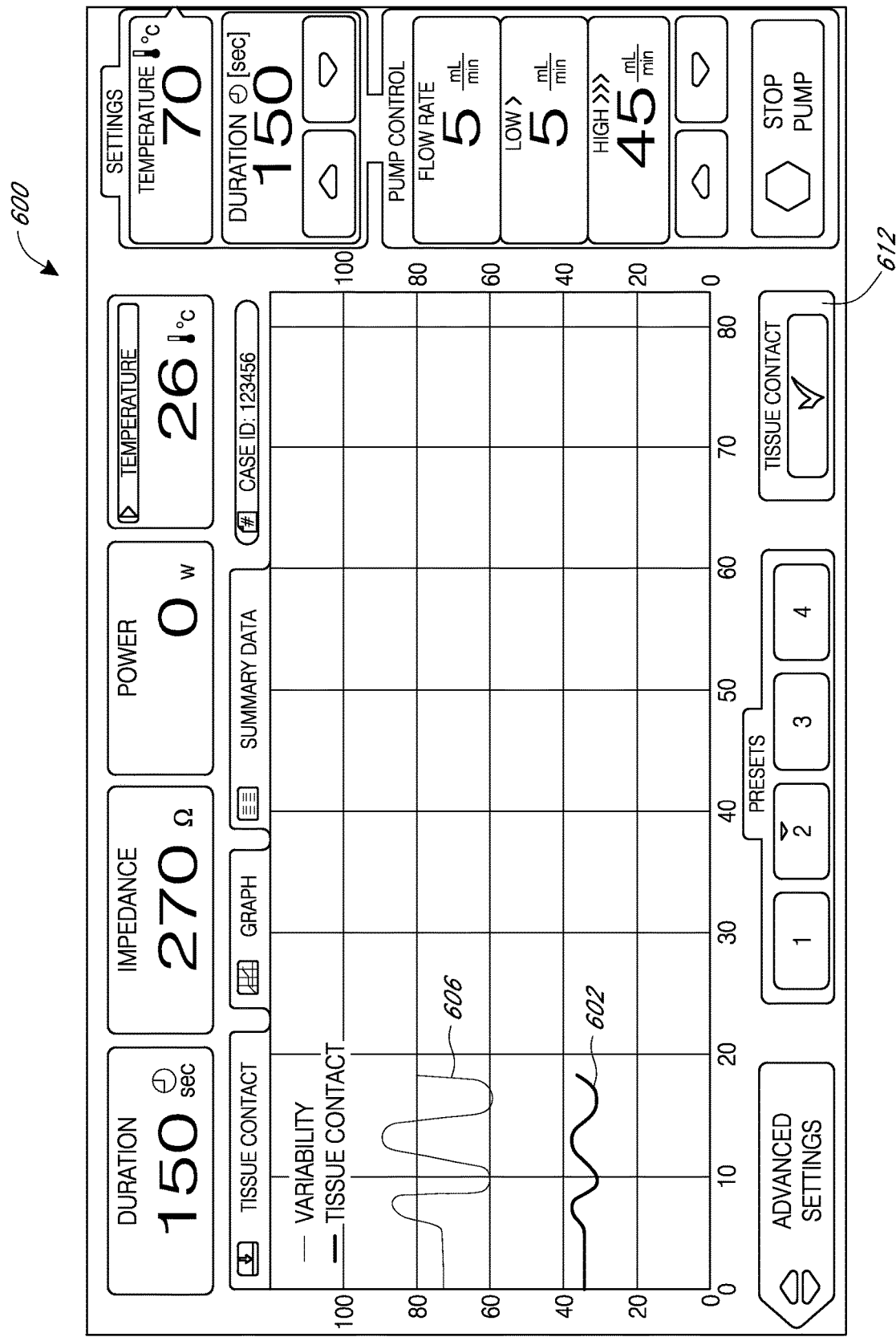
FIG. 6 is an embodiment of a user interface of a display of an energy delivery module.

FIG. 6 is an embodiment of a user interface 600 of a display (for example, one of I/O components 44 of the energy delivery module 40 (for example, a radiofrequency generator). As shown, the user interface 600 may display various parameters of the energy delivery system 10, such as duration settings, impedance measurements, power settings, temperature measurements or settings, irrigation settings, and one or more signals or graphs. The user interface 600 may comprise a touchscreen display that facilitates receipt and actuation of user inputs and controls. For example, the user interface 600 comprises actuatable areas or inputs to stop and start an irrigation pump or adjust duration or irrigation flow settings (indicated by up and down arrows). The user interface 600 also includes options to toggle between various preset operational and/or display configurations.

In the illustrated embodiment, the user interface 600 is configured to display the variability index signal 606 and/or other signals indicative of tissue contact, such as the $\text{Mov\_avg}\,V_{rad}(n)$ signal 602. In some embodiments, the user interface 600 is configured to display any or all of the signals shown in FIGS. 4, 5A and 5B. A user may be able to observe or determine that contact has occurred and/or the amount or sufficiency of contact based on an observance of the variability index.

In the illustrated embodiment, the user interface 600 also includes a tissue contact indicator 612 to provide an indication of tissue contact. In some embodiments, the tissue contact indicator 612 may provide a qualitative indication of a level of contact. The qualitative indication may be provided in the form of a color, a textual indication, a numerical or percentage-based indication and/or a graphical indication. A color of the indicator 612 may change based on the quality of contact. For example, a red color may indicate poor or weak contact, a yellow color may indicate questionable or medium contact, and a green color may indicate "good" contact. In some embodiments, the color indication may be supplemented with an additional indicator (a checkmark in the illustrated embodiment) to indicate "excellent" contact.

The qualitative assessment may be determined based on identified thresholds. For example, threshold ranges may be identified for different amplitudes of the variability index, with the qualitative assessment being determined based on which threshold range the variability index falls within. The thresholds may be predetermined or may be determined in real-time based on recent historical measurements. The thresholds may be set automatically (using software) or manually. In some embodiments, the thresholds are automatically adjustable based on real-time parameters or recent historical measurements (for example, average historical peak-to-peak deflection amounts in the variability index or other variability output). For example, the thresholds may be adjustable based on location, tissue type, patient-specific data (for example, average historical peak-to-peak deflection amounts in the variability index or other variability output for that patient). The thresholds may be set to take into account historical measurements. Alternatively, thresholds may be defined based on the frequency content of the variability index or based on the peak-peak amplitude of the $\text{Mov\_avg\_}V_{rad}(n)$ signal 504. As shown in FIGS. 5A and 5B, the variability index signal 506 has a more random aspect and lower amplitudes when the electrode is not in contact with tissue. Conversely, as shown in FIG. 5B, when the electrode is in contact with tissue, both the peak-peak amplitude of $\text{Mov\_avg\_}V_{rad}(n)$ signal 504 and that of the variability index signal 506 are higher. Similarly, the frequency content of the variability index signal 506 correlates with the respiratory artifact seen in traces 502 and 504, as the catheter, due to its better contact with the heart wall, follows the motion of the heart during the patient's respiration.

Figure 7:
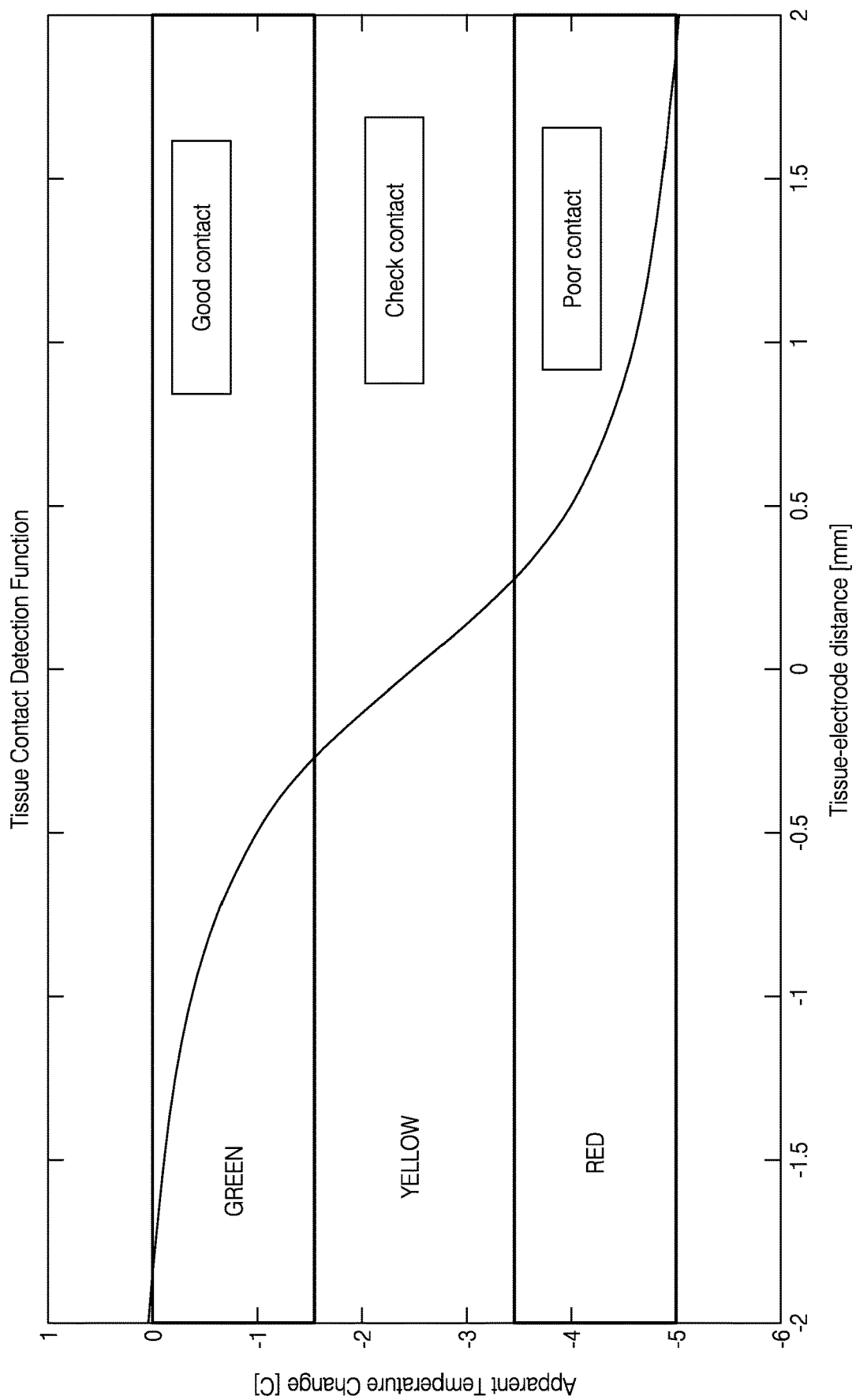
FIG. 7 is a graph of a contact detection function and schematically illustrates that a qualitative assessment of contact may be determined for different ranges of measurements and provided to a user.

FIG. 7 is a graph of a contact detection function and schematically illustrates that a qualitative assessment of contact may be determined for different ranges of measurements and provided to a user. In some embodiments (such as for electrode-tissue distances within the range of −2 mm to 2 mm), the detection model as follows:

$$\Delta T_{Apparent} = -2.5 - \frac{6}{\pi} * \arctan(3d),$$

where d is the distance between the antenna/electrode and tissue expressed in mm. The distance between electrode and tissue can be computed as $$d = -\frac{1}{3} * \tan\left[\frac{\pi}{6} * (\Delta T_{Apparent} + 2.5)\right].$$

Alternatively, lookup tables can be used to define the relationship between the electrode-tissue distance and the apparent temperature change. The lookup tables may be associated with processor 46 and can be implemented in hardware and/or software. In some embodiments, quality of contact may be determined, and an output or indication may be provided on a display that is indicative of the level or quality of contact. Other approximations of the relationship between electrode-tissue distance and apparent temperature change may also be used in other embodiments.

The contact detection function may be used to detect tissue contact by using a threshold that indicates contact or no contact and an indicator may be displayed on a display. In some embodiments, a piecewise linear threshold can be used to provide a gradual indication about the level, amount or quality of contact. For example, the gradual indication can be poor, medium, good and excellent level of contact. In some embodiments, apparent temperature changes may be determined from the variability index signal or other output. FIG. 7 identifies ranges of apparent temperature change values that may be identified as indicative of poor contact, questionable contact, and good contact. Although not illustrated in color because the figures are represented in black and white, textual labels have been added to indicate colors (red for poor contact, yellow for questionable contact and green for good contact). Alternatively, a quantitative measure of the level of contact between electrode and tissue may be provided by displaying a corresponding bar graph. For example, the bar graph may use at least, but not necessarily limited to, three (for example, three, four, five, six, or more) levels of contact between electrode and tissue. A binary output may be used in some embodiments. In some embodiments, only a qualitative measure is provided and not a quantitative measure.

Figure 8:
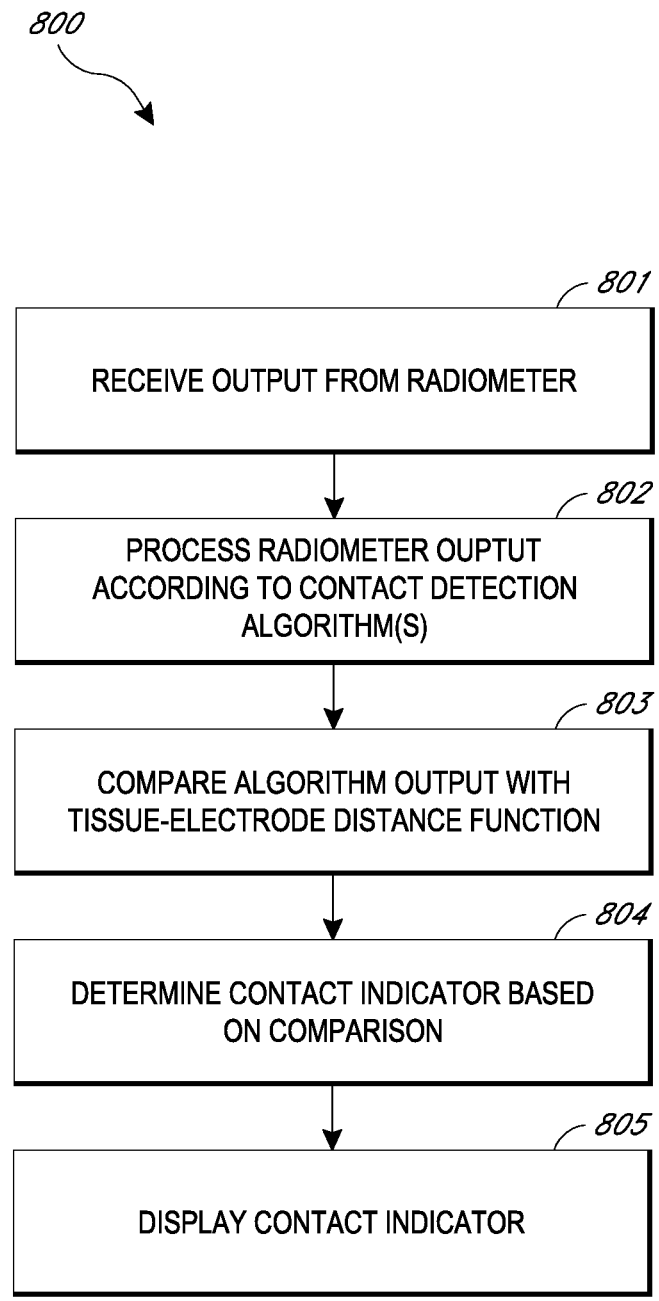
FIG. 8 is a flow diagram of an embodiment of a tissue contact detection process.

FIG. 8 illustrates a flow diagram of an embodiment of a process for tissue contact detection configured to be executed by the processor 46 or another computing device. Prior to step 801, radiometer 60 receives microwave emissions indicative of dielectric differences between blood and tissue (for example, endocardial tissue). At step 801, processor 46 acquires the output of radiometer 60, which may be a voltage signal. At step 802, processor 46 processes the radiometer output according to a tissue contact detection algorithm, such as any of the processing techniques discussed in connection with FIGS. 3-5. At step 803, processor 46 compares the output of the tissue contact detection algorithm with a tissue-electrode distance function, such as that described in connection with FIG. 7 or another suitable function. At step 804, processor 46 determines a contact indicator based on the comparison performed in step 803 and generates an output indicative of the tissue-electrode distance, or of the amount of tissue contact. The output may be qualitative and/or quantitative. As described in connection with FIG. 7, such output may turn ON a green indicator if contact is good, a yellow indicator if contact is mediocre, or a red indicator if contact is poor. Other alternative indications or outputs are possible as further described herein. At step 805, the indicator or other output is displayed on the user interface 600. As an example, the output of the comparison at step 804 may be displayed by contact indicator element 612 of user interface 600. Any of the steps of the tissue contact detection 800 may be optional, or omitted.

In some embodiments, signal processing may be implemented to remove or ignore the "non-contact" peak-to-peak amplitude from the assessment and/or to apply a scaling factor based on the non-contact" peak-to-peak measurements. In some embodiments, variability may be detected and reduced or accounted for during processing to further enhance contact assessment. Variability may be cause by respiratory artifacts (for example, respiratory rate) and/or cardiac artifacts (for example, heart movement), with the amount of variability caused by each type of artifact dependent on location.

Figure 9:
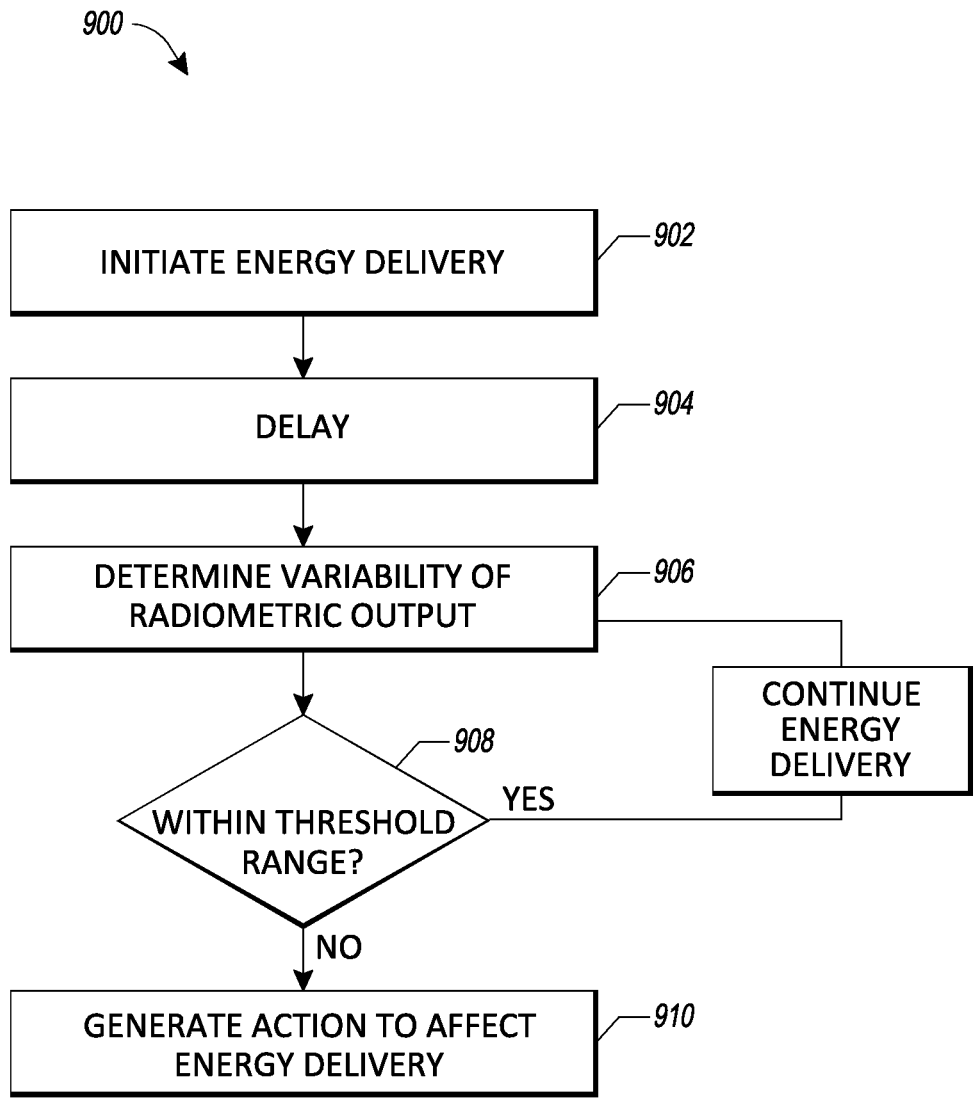
FIG. 9 is a flow diagram of an embodiment of a catheter motion or dislodgment sensing or monitoring process.

FIG. 9 illustrates one non-limiting embodiment of a flow diagram of a catheter motion or dislodgement sensing or monitoring process 900. The process 900 begins when the processor 46 initiates energy delivery by the catheter or other energy delivery device or medical instrument (Block 902). In some embodiments, the processor 46, upon execution of program instructions stored in memory, continuously monitors the output (for example, $V_{rad}$ signal) received from a radiometer of an energy delivery device (for example, RF ablation catheter) during energy delivery (for example, a cardiac ablation procedure) to monitor catheter movement or loss of contact or sudden dislodgement. In one embodiment, the monitoring is implemented as a software sensor. During a normal ablation, for example, heating of the tissue would cause the $V_{rad}$ signal to drop since it is inversely proportional to temperature. In some embodiments, the processor 46 continuously determines a variability of the radiometric output (for example, calculates a slope of the $V_{rad}$ signal) in real time at a periodic time interval (Block 906), for example 0.1-2 seconds, 0.1-0.5 seconds, 0.5-1.5 seconds, 0.5-1 second, 1-2 seconds, or overlapping ranges thereof. The slope calculations may be initiated after a predetermined delay (Block 904) following initiation of energy delivery at Block 902 (for example, 0.5 to 2 seconds). In some embodiments, the processor 46 determines whether the variability is within a threshold range (Block 908). For example, the processor 46 may compare the calculated slope to an expected value. If the slope is within an expected threshold range, the energy delivery (for example, cardiac ablation) procedure may continue and the process loops back to Block 906. If the variability is determined to be outside of an expected threshold range, the processor 46 may generate an action intended to affect (for example, alter, adjust, terminate) the energy delivery procedure (Block 910).

For example, if the calculated slope ever begins to move in a positive direction by some magnitude (any slope greater than zero, for example), or is out of an expected range, one could assume that the catheter or other medical instrument moved to a cooler place in the tissue, or it came off (lost contact with) the tissue. The change in slope could warn the physician that something moved. If the $V_{rad}$ signal is displayed, the physician or other clinician could visually observe the change in slope. In some embodiments, the processor 46 is configured to generate a visual or audible alert or notification. The alert or notification could automatically terminate energy delivery and reduce or terminate irrigation or could cause the user to terminate energy delivery and reduce or terminate irrigation. In some embodiments, the processor 46 or user could monitor for abnormally low heating using the $V_{rad}$ signal and the radiometer slope value of the individual catheter (50% of nominal expected temperature rise, for example). In some embodiments, sudden changes in slope may also or alternatively be used to alert for too much tissue contact that may result in undesired tissue perforations or in overheated energy delivery.

Reflectometry for Tissue Type Detection and Radiometer Enhancement

In some embodiments, microwave radiometers can detect tissue contact based on recognizing differences in properties (for example, dielectric properties) of the surrounding medium (for example, blood vs. heart tissue). For example, dielectric constants may differ such that the characteristic impedance of an antenna, $Z_A$, of the ablation catheter changes as the antenna comes in contact with, or loses contact with, target tissue. In some embodiments, the reflection coefficient Γ of an antenna loaded with different tissue types can provide an indication of the dielectric properties of such tissue, which can be utilized in determining tissue type. In cardiac applications, for example, tissue type determination might include classifying normal cardiac tissue vs. infarct vs. previously-ablated tissue. Other types of tissues, such as scar tissue, connective tissue, vascular tissue and pulmonary veins may be detected as well. Presence of adjacent tissues, such as lung, or esophagus, can also be detected.

In accordance with several embodiments, an ablation catheter (for example, radiofrequency ablation catheter 100) comprises a miniature microwave reflectometer configured to determine dielectric-dependent reflection coefficient measurements. As used herein, the terms "miniature" and "miniaturized" shall be given their ordinary meanings and shall also include structures sized, for example, such that they are compatible with existing radiofrequency ablation catheters. In some embodiments, a miniaturized reflectometer may be sized such that it fits on a circuit board or ceramic substrate with dimensions of 3 mm×12 mm. In one embodiment, a miniaturized design has dimensions of up to 2 mm×8 mm. In various embodiments, miniaturized designs have an area of between 10 mm$^2$ and 40 mm$^2$ (e.g., between 10 and 20 mm$^2$, between 15 and 30 mm$^2$, between 20 and 40 mm$^2$, or overlapping ranges thereof). A reflectometer is a circuit that directly measures reflection coefficient. The reflectometer could be used in real-time during ablation procedures (for example, cardiac ablation) to classify different tissue types, which may be helpful in contact sensing applications (for example, whether a tip of the ablation catheter is in contact with a target tissue to be ablated (for example, vessel or organ wall) or to confirm whether an ablation procedure has been successful). For example, the reflectometer can be used to determine between normal infarct and ablated tissue by correlating changes in the measured reflection coefficient to tissue type. This procedure could be performed with just a radiometer using antenna impedance but because changes in impedance might be fairly subtle, measurements (and accordingly, tissue type determination) may be more accurate using just changes in reflection coefficient directly measured by the reflectometer without using antenna impedance measurements.

Several embodiments of the reflectometry systems and methods described herein are particularly advantageous because they include one, several or all of the following benefits: (i) allow for decoupling of contact sensing algorithms and temperature measurements (for example, the radiometric ablation system can purely use changes in reflection coefficient measured by the reflectometer to perform contact sensing and purely use the radiometer for measuring tissue temperature); (ii) little or no effect on normal performance of the radiometer by performing measurements while the radiometer is switched to a reference mode; (iii) shorter procedure times due to increased efficiency; (iv) reduction in likelihood of undesired damage to tissue not intended to be ablated or otherwise treated; (v) increases accuracy of contact sensing and determination functionality; (vi) increase in likelihood of success of treatment; (vii) measurement of both the magnitude and/or phase of a reflected signal (or reflection coefficient); (viii) additional information regarding tissue confirmation using multiple frequency approaches; (ix) automatic adjustment of temperature measurements; (x) sensitivity to subsurface changes in tissue properties, allowing detection of said changes; (xi) ability to be multiplexed with lower-frequency RF and electrogram signals.

In accordance with several embodiments, the radiometric ablation system may advantageously use dynamically changing reflection coefficients measured by the reflectometer during heating to provide a more accurate temperature measurement response as feedback to adjust parameters of the heating procedure, thereby improving efficiency and efficacy. For example, magnitude information of the reflection obtained from the reflectometer may advantageously be utilized to enhance the accuracy of radiometric temperature measurements of a radiometric ablation catheter system. The equation for the amount of power P received by a radiometer is reproduced below:

$$P=k*Df*[(1-D^2)*T_{Tissue}+D^2*T_{Radiometer}],$$

where k is Boltzmann's constant, Df is the bandwidth of the radiometer system, D is the reflection coefficient between the antenna and radiometer, $T_{tissue}$ is the noise temperature received by the antenna and $T_{radiometer}$ is the noise temperature emitted by the radiometer. If during an ablation, for example, there are significant uncompensated changes in the reflection coefficient seen by the radiometer, this may have deleterious effects on the temperature accuracy. In several embodiments, adding a correction for reflection coefficient may be utilized to improve radiometer accuracy.

In addition, a typical radiometer can only determine the magnitude of the reflection coefficient and not the phase. A miniature microwave reflectometer positioned within an ablation catheter may advantageously measure both the magnitude and/or phase of a reflected signal (or of the reflection coefficient). More information about the tissue being evaluated provides more accuracy in determining tissue type. The reflectometer may be positioned at any location within the ablation catheter or other tissue treatment device or medical instrument. In one embodiment, the reflectometer is positioned at a distal end or tip of the ablation catheter.

Because differences in the reflection coefficient among various tissue types might be subtle, it may be helpful to measure both the magnitude and phase of the reflection coefficient over a band of frequencies. In several embodiments, the reflectometer facilitates reflection coefficient measurements over a range of frequencies, or at least of a frequency different from the frequency of the radiometer. The reflectometer circuit illustrated in FIG. 11B provides an example of how multi-frequency reflection coefficient measurements may be performed. Performing measurements over a range of frequencies using a radiometer alone would likely require use of a multi-band radiometer.

Figure 10A:
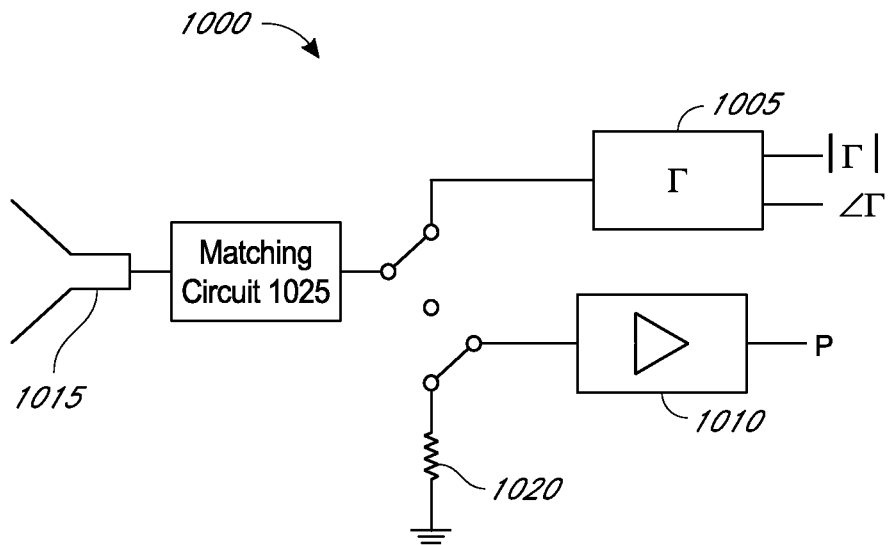
FIGS. 10A and 10B schematically illustrate embodiments of a reflectometer used in conjunction with a radiometer circuit.

FIG. 10A schematically illustrates an embodiment of a radiometric ablation catheter 1000 including a reflectometer 1005 for determining reflection coefficients and a radiometer 1010 for determining temperature measurements at a depth. The radiometer 1010 continuously switches back and forth between an antenna 1015 and a reference load 1020 to correct for variations in local temperature of the circuitry. During the time that the radiometer 1010 is making its reference load measurements, a reflectometer switch 1012 may be toggled to connect the antenna 1015 (through an appropriate matching network 1025) to the reflectometer 1005 to measure reflection coefficients. The switching or toggling of the reflectometer switch 1012 may be controlled by a clock under control of a processor (for example, within the ablation catheter 100 or other medical instrument 20, or within the energy delivery module 40).

Figure 10B:
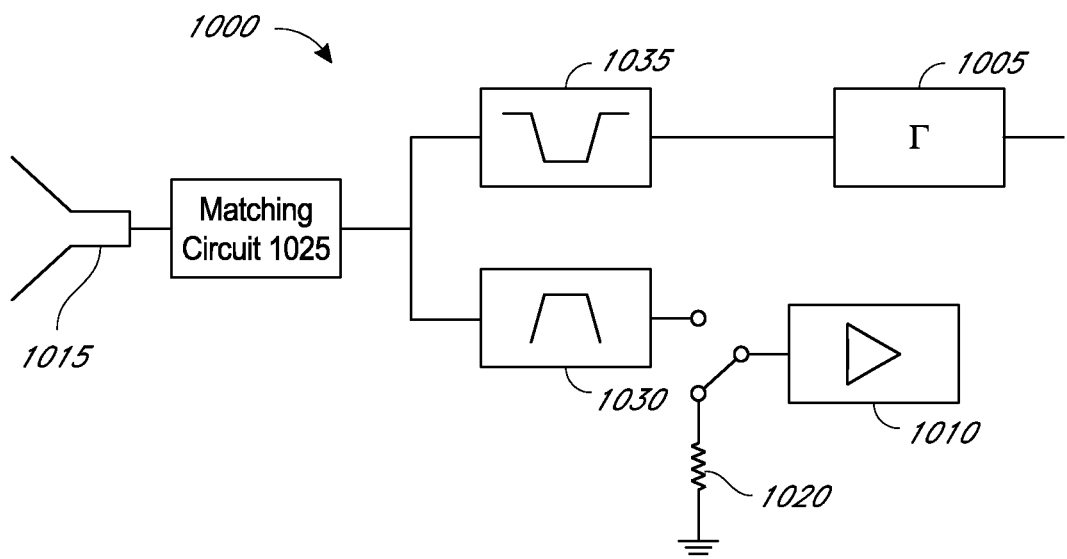

FIG. 10B illustrates another embodiment of a radiometric ablation catheter 1000 including a reflectometer 1005 for measuring reflection coefficients. Radiometers are designed to be very sensitive to signals in its frequency band. The illustrated embodiment includes a diplexer including a band pass filter 1030 and a band stop filter 1035. The band pass filter 1030 allows signals in the frequency band of the radiometer 1010 (e.g., 3.5 GHz to 4.5 GHz for an operating radiometer frequency of 4 GHz) to pass through to the radiometer 1010 while the band stop filter 1035 rejects signals in the frequency band of the radiometer 1010 to prevent interference with the radiometer circuit, while allowing signals of other frequencies to pass through to the reflectometer 1005. This implementation allows the reflectometer 1005 and the radiometer 1010 to share the same antenna, thereby facilitating simultaneous measurement of reflection and temperature. The reflectometer 1005 would have to be operated at a different frequency than the radiometer 1010 in this implementation. In some embodiments, as discussed in more detail later herein, interpolation could be used to estimate reflection coefficients at the operation frequency of the radiometer 1010.

Figure 11A:
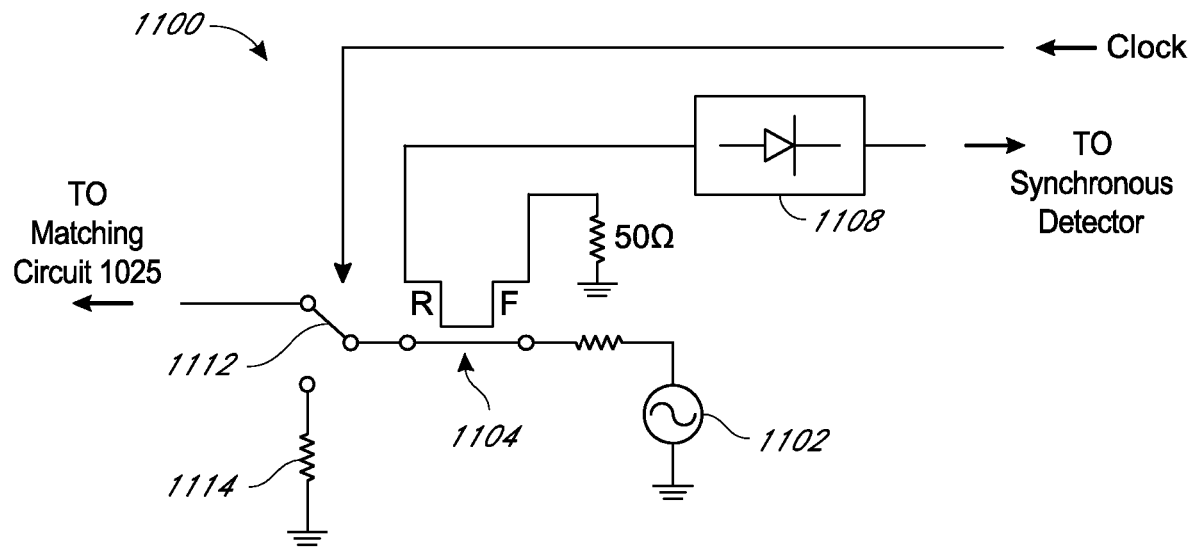
FIGS. 11A and 11B schematically illustrate embodiments of reflectometer circuits.
Figure 11B:
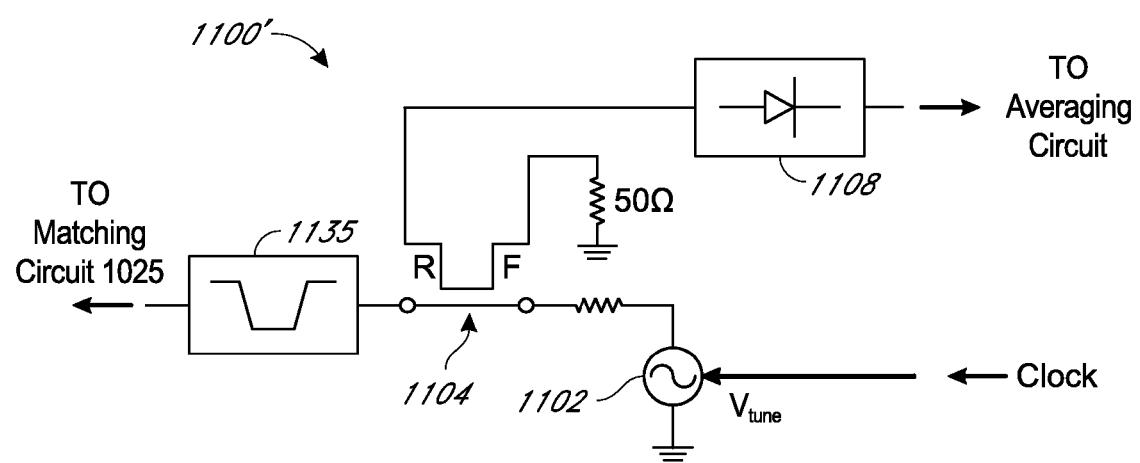

FIG. 11A illustrates another embodiment of a reflectometer circuit 1100 of a radiometric ablation catheter. The reflectometer circuit 1100 includes a voltage controlled oscillator 1102, a directional coupler 1104 and a magnitude detector 1108, for example a Schottky diode detector. The directional coupler 1104 is configured to sample a microwave signal and discriminate between forward-traveling power (waves or signals) and reverse-traveling power (waves or signals). The output of the directional coupler 1104 can be fed into the magnitude detector 1108 to determine the magnitude of the reflection coefficient because the ratio of the forward-traveling power to the reverse-traveling power is essentially the reflection coefficient. In several embodiments, the reflectometer is an active device that requires a source of microwave energy to feed the reflectometer circuit 1100. Phase detector circuitry may also be utilized instead of a diode detector to perform measurements of the reflected phase of the antenna.

The reflectometer circuit 1100 includes a switch 1112 to toggle between a reference load 1114 (for example, 50Ω resistor), which provides a very low reflection condition and the antenna of the radiometric ablation catheter, which provides a non-zero reflective power signal. A synchronous detector may be used to subtract the two signals from each other to determine the reflection coefficient. For phase detection, the load might comprise a high-reflection load with a known phase shift, such as, for example, an open or short circuited transmission-line. In some embodiments, the reflectometer circuit 1100 assumes that the forward-traveling power is constant and only measures the reverse-traveling power.

FIG. 11B illustrates an embodiment of a dual-frequency reflectometer circuit 1100'. The implementation is similar to the reflectometer circuit 1100 illustrated in FIG. 11A except that a clock signal may be used to vary the frequency of the voltage-controlled oscillator 1102 between two different frequencies outside of the in-band radiometer frequencies (for example, 3 GHz and 5 GHz for a 4 GHz radiometer). Interpolation may then be used to estimate the reflection coefficients at the operating frequency of the radiometer using an averaging circuit or other devices or methods (analog and/or digital). The estimated reflection coefficients may advantageously be used to adjust or correct radiometric temperature measurements for improved accuracy. In other implementations, more than two different frequencies (for example, 3, 4, 5, 6, or more than 6) may be used to provide more accurate interpolation. In addition to radiometric temperature improvement, a multi-frequency approach may allow more precise tissue characterization schemes to be implemented. For example, in a dual frequency case, the trajectory of the magnitude (and/or phase) of the reflection coefficient as the frequency changes from 3 to 5 GHz for example, may provide further information regarding tissue composition.

In accordance with several embodiments, the reflection coefficient measured by the reflectometer is a function of the impedance of the antenna as loaded down by the tissue. For example, differing tissue types may have a different value for the relative dielectric constant, which would have corresponding differences in the wavelength in the tissue, and subsequently the impedance of the antenna would change. Considering, for example, the simple case of a half-wavelength dipole antenna designed for resonance (optimal impedance match) in blood. Such an antenna will likely shift off of resonance (and thus change its impedance) when brought in the presence of a different media (such as unablated heart tissue, etc.) due to the different dielectric constant. These changes may then be detected via the reflectometer measurement. Additionally, the matching network 1025 may be utilized to enhance the changes in impedance as measured by the reflectometer circuit 1100, 1100'.

In accordance with several embodiments, a processor, controller, or other computing device (for example, processor 46) is configured to receive the measured reflection coefficient output from the reflectometer 1005 and to determine or identify a tissue type based on one or more reflection coefficient measurements. In some embodiments, the processor is further configured to determine whether the distal end of the elongate body is in contact with a target tissue to be heated (for example, ablated) based on the determined tissue type. The determined tissue type may, for example, provide information regarding whether an ablation procedure at a target ablation site has been successful. The processor may also execute a code module or set of instructions to automatically adjust or calibrate temperature measurements obtained by the radiometer based, at least in part, on the reflection coefficient measured, calculated or otherwise determined by the reflectometer, thereby enhancing operation of the radiometer.

The type of tissue identified by the processor may be, for example, non-ablated normal tissue, infarct tissue, or ablated tissue. The identified tissue type may provide confirmation of a successful ablation or an indication that the ablation was not effective and additional ablation time is required. The tissue may be cardiac tissue or tissue of other organs or vessels. In some embodiments, the tissue type may be determined to be blood or a tissue wall to facilitate determination of contact prior to ablation.

Figure 12A:
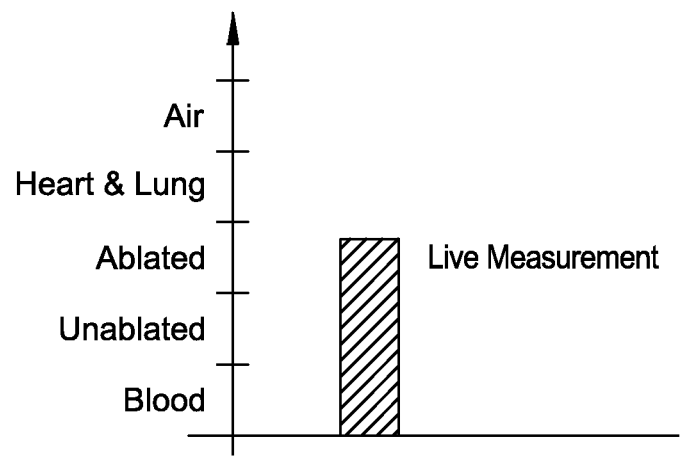
FIGS. 12A and 12B are plots illustrating how tissue type can be determined from measured reflection coefficients and displayed to a user.
Figure 12B:
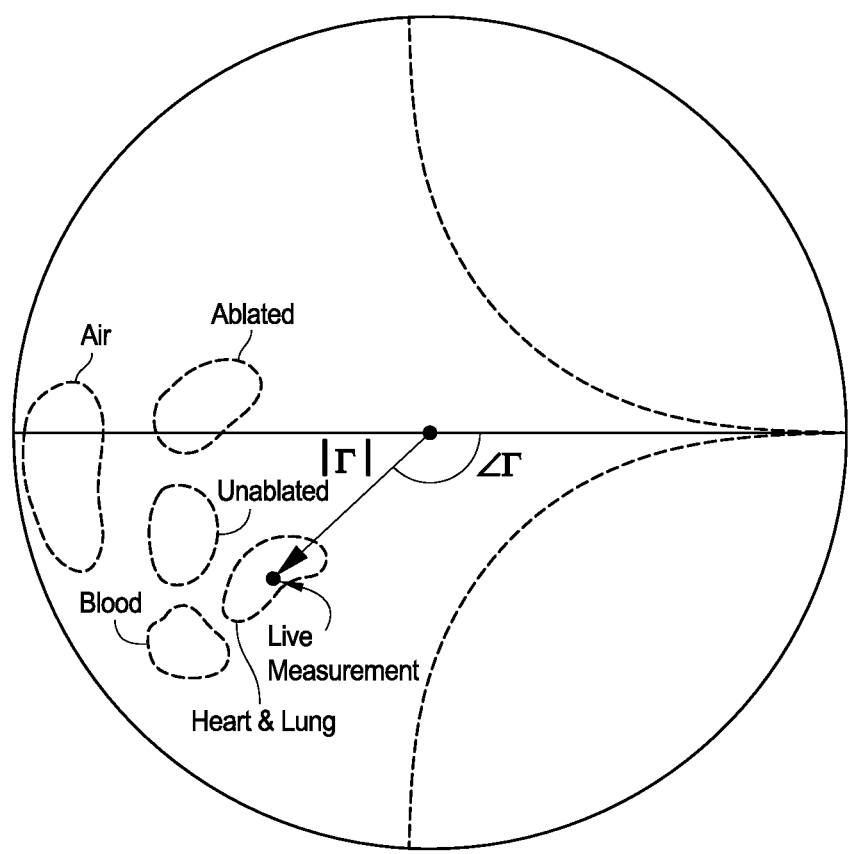

In some embodiments, the processor is configured to provide an output indicative of the tissue type and/or an output indicative of contact with tissue. The output may be provided textually (words, numbers and symbols) and/or graphically (check marks, colors). For example, output indicative of contact can indicate that contact has occurred (for example a Yes/No output or a checkmark) or can provide a qualitative assessment of the level of contact (for example, excellent, good, poor, no contact indicated textually and/or visually, such as by using colors). The output may be displayed on a display in communication with the processor. For example, in one embodiment, the output is displayed on a display of the energy delivery module 40 (for example, a generator). For a magnitude-only detection scheme, thresholds delineating the magnitude expected for different antenna loading conditions (and corresponding tissue impedance responses indicating tissue type, ablation state and contact condition) may be determined and compared with live magnitude measurements. An example output for a display is shown in FIG. 12A. For a magnitude and phase reflectometer, regions of magnitude/phase combinations that indicate specific tissue types may be delineated on a Smith Chart or polar plot, with live magnitude/phase measurements plotted to determine the current tissue type the antenna is loaded by. An example output for a display is shown in FIG. 12B.

In some embodiments, the system comprises various features that are present as single features (as opposed to multiple features). For example, in one embodiment, the system includes a single ablation catheter with a single antenna, a single energy delivery radiofrequency electrode and a single microwave radiometer. The antenna and radiofrequency electrode may form a single, unitary, or integral, construct at the distal end of the catheter. A single thermocouple (or other means for measuring temperature) may also be included. The system may comprise a single reflectometer as described herein. Multiple features or components are provided in alternate embodiments.

In some embodiments, the system comprises one or more of the following: means for tissue modulation (for example, an ablation or other type of modulation catheter or delivery device), means for generating energy (for example, a generator or other energy delivery module), means for connecting the means for generating energy to the means for tissue modulation (for example, an electrical, mechanical, or electromechanical interface or input/output connector or other coupling member), means for displaying (for example, a monitor, screen or user interface), etc.

Frequency Multiplication for Radiometer Systems

Several embodiments of the invention relate to systems and methods for achieving greater sensing depths or volumes for tissue characterization performed by a radiometer system without having to replace or adjust the radiometer of the radiometer system. Embodiments of the systems and methods disclosed herein may be used with existing back-end radiometer systems. The systems and methods may allow for increased sensing depths of a radiometric cardiac ablation catheter or other tissue treatment or diagnostic device having a radiometer. Frequency multiplication techniques may be provided in a front end to facilitate greater sensing depth while maintaining an operating frequency of the back-end radiometer system. Maintaining the operating frequency of the back-end radiometer system allows for reduced sizes and miniaturization of electronic components. Several embodiments of the invention utilize a given frequency and use frequency multiplication techniques to achieve higher frequency radiometer circuits that are of reduced size (e.g., "miniaturized").

Several embodiments of the frequency multiplication systems and methods described herein are particularly advantageous because they include one, several or all of the following benefits: (i) providing minimal changes to existing radiometer system while extending sensing depth, (ii) does not require replacement of an existing radiometer in a previously-designed radiometer system; (iii) reduced size for back-end stage of a radiometer system, since it operates at a higher frequency, (iv) provides noninvasive temperature measurements; (v) size of the distal portion of the medical instrument housing the radiometer system may be kept the same or reduced; and (vi) reduced sensitivity to back-to-front leakage that may lead to instabilities in the radiometer system or circuit, as the front end would tend to reject higher frequency signals at its input.

In some embodiments, characterization of tissue or measurement of tissue parameters at greater depths than may be achieved by a built-in radiometer of a radiometer system (such as a radiometer of a cardiac ablation catheter) may be desired. For example, ablation lesions may be formed that extend to depths greater than the built-in radiometer is capable of sensing, due to the operational frequency of the radiometer. As another example, ablation lesions may cover a larger volume of tissue than the built-in radiometer is capable of sensing at a given position. The radiometer could be replaced with a lower frequency radiometer (as lower frequencies provide increased sensing depth); however, this would require a significant change to the existing radiometric system. In accordance with several embodiments, sensing over a larger volume (for example, greater depth) is possible while maintaining the existing radiometer circuitry operating at a higher frequency (for example, without requiring replacement of the existing radiometer or without requiring a significant change to the back end radiometer system).

Reducing the operational frequency of the radiometer would also have the effect of increasing a length of a quarter-wave stub of the radiometer circuit that filters out signals other than those in the microwave range to be processed by the radiometer. For embodiments where the radiometer system is in a medical instrument intended to be used within a vessel, body lumen or body cavity (such as a cardiac ablation catheter), smaller sizes may be desired or required. Accordingly, by designing an antenna to operate at a lower frequency and then multiplying up the frequency to the operational frequency of the radiometer, the size of the distal portion of the medical instrument housing the radiometer system may be reduced (for example minimized) or kept the same while still providing increased sensing depth. In various embodiments, the length of the quarter-wave stub is less than about 20 mm (for example, 20 mm, 19 mm, 18.75 mm, 18 mm, 17.5 mm, 17 mm, 16 mm, 15 mm). In one embodiment, the length of the quarter-wave stub is less than 15 mm. In another embodiment, the length of the quarter-wave stub is less than 10 mm. In various embodiments, the quarter-wave stub may be implemented in conjunction with irrigation tubing extending along and within a lumen of an ablation catheter, as described in greater detail in U.S. Pat. No. 7,769,469 and U.S. Patent Publication No. 2010/0076424, the entirety of each of which is hereby incorporated by reference herein.

In one embodiment, the larger volume interrogation can be achieved using a low-noise frequency multiplier module that provides an initial stage, or front end, of low noise amplification and also multiplies the frequency to a higher harmonic (such as a frequency doubler or tripler). The remaining stage(s) of the radiometer circuit or system may be implemented at the higher frequency, potentially allowing significant miniaturization of the electronics, which may be particularly advantageous for cardiac ablation catheters or other medical instruments operating in passages, lumens or cavities with limited space.

Figure 13:
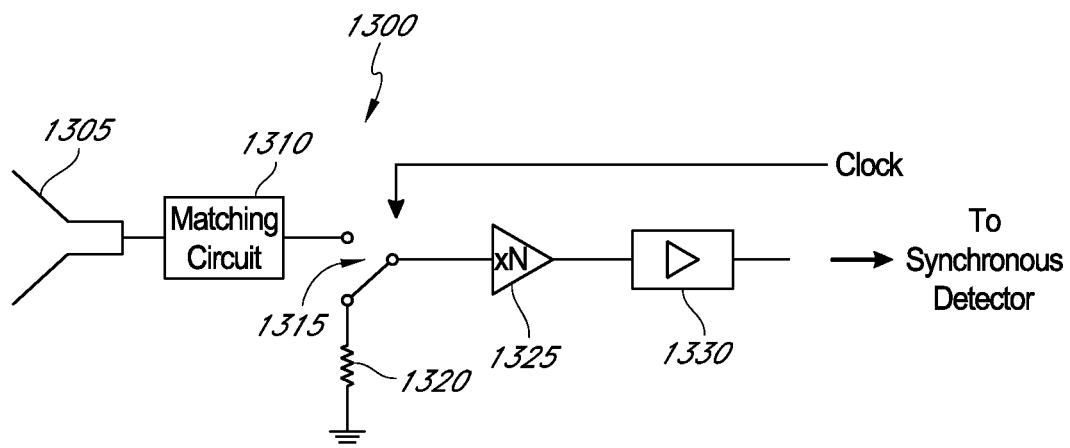
FIG. 13 is a schematic circuit diagram of an embodiment of a front end of a low noise frequency multiplier for use in a radiometer system.

FIG. 13 is a schematic circuit diagram of an embodiment of a frequency multiplication system or module 1300 for use in a radiometer system, such as the radiometer 60 of the ablation catheter 100 of FIG. 2 or the medical instrument 20 of FIG. 1. The frequency multiplication system 1300 comprises an antenna 1305, a matching circuit 1310, a switch 1315, a reference load 1320, and a frequency multiplier 1325. The output of the frequency multiplier 1325 is fed to a radiometer circuit 1330, such as the radiometer 60 if FIGS. 1 and 2.

The antenna 1305 may be the same antenna used in a pre-existing radiometer system without frequency multiplication, or may be a separate and distinct antenna. The antenna 1305 may be configured to operate at a frequency different from (for example, lower than) the operational frequency of the radiometer circuit 1330. In some embodiments, the operational frequency of the antenna 1305 is a fraction (for example, $\frac{1}{10}$, $\frac{1}{9}$, $\frac{1}{8}$, $\frac{1}{7}$, $\frac{1}{6}$, $\frac{1}{5}$, $\frac{1}{4}$, $\frac{1}{3}$, $\frac{1}{2}$) of the frequency of the operational frequency of the radiometer 1330. The lower frequency of the antenna 1305 advantageously facilitates deeper sensing depth for tissue characterization (for example, temperature measurements, tissue type determinations). The deeper sensing depth may facilitate increased accuracy in contact sensing, lesion volume or gap measurements, tissue type determinations and/or other analyses. In some embodiments, for a radiometer having an operational frequency of 4 GHz, the antenna 1305 may be designed to receive signals at a frequency of about 1 GHz, 1.33 GHz or 2 GHz. Of course, radiometers having operational frequencies of other than 4 GHz may be used as desired and/or required.

In some embodiments, the matching circuit 1310 comprises an impedance matching network, such as a lossless or substantially lossless impedance matching network, configured to match the output impedance from the antenna 1305 with the load impedance of the remaining system or subsequent circuit element(s). In various embodiments, the matching circuit 1310 comprises one or more of the following: matching stubs, lengths of thru transmission lines, quarter-wavelength transformers, and lumped elements of inductors and/or capacitors. The switch 1315 may comprise a microwave solid-state switch or other type of switch controlled by a clock signal that is regulated by a processor (for example, processor 46). The switch 1315 dithers the input to the radiometer 1330 between the antenna output (through the matching circuit 1310) and the reference load 1320, similar to a baseline radiometer system (for example, a singleband Dicke radiometer) without a frequency multiplier. The reference load 1320 provides an internal reference temperature that can be compared with an actual radiometric measurement to determine tissue temperature based on the comparison. In some embodiments, noise power at the antenna 1305 is compared to a reference and offset errors common to both the reference load 1320 and antenna 1305 cancel at the output, thereby providing a more accurate result.

The common terminal of the switch 1315 is fed into the frequency multiplier 1325. The frequency multiplier 1325 may be configured to generate an output signal having a frequency that is a multiple of the input signal frequency from the antenna 1305. If the input frequency is $f_0$, then the output signal of the frequency multiplier 1325 has a frequency of $Nf_0$. The frequency multiplier 1325 may double, triple, quadruple or otherwise multiply the frequency of the antenna 1305. In one embodiment, the frequency multiplier 1325 is a doubler. In another embodiment, the frequency multiplier 1325 is a tripler. In another embodiment, the frequency multiplier 1325 is a quadrupler. The frequency multiplier 1325 may facilitate the output of low-noise signals to the radiometer 1330.

In various embodiments, the frequency multiplier 1325 comprises a low-pass filter configured to pass the fundamental signal and reject any higher harmonics, a nonlinear device (such as a step recovery diode or a varactor) configured to produce harmonics, a bandpass or high-pass filter configured to pass only a desired harmonic and reject all other signals, and/or one or more matching circuits. The matching circuit 1310 may be considered a component of the frequency multiplier 1325 in some embodiments. In one embodiment, the varactor comprises variable capacitance and series resistance. The radiometer circuit 1330 may comprise low-noise amplification, filtering and/or power detection elements, such as a synchronous detector (not shown) configured to facilitate determination of temperature or other measurements and/or contact.

In accordance with several embodiments, the frequency multiplication circuit 1300 is designed to operate over a frequency band that is suitable (for example, optimal) for radiometric applications. As one example, the front end (for example, antenna 1305) could operate at 1.8 to 2.2 GHz, which would correspond to a 3.6 to 4.4 GHz band for the back end (for example, radiometer 1330), with the frequency multiplier 1325 acting as a doubler. As another example, the front end could operate at 1.2 to 1.467 GHz, which would correspond to a 3.6 to 4.4 GHz band for the back end, with the frequency multiplier 1325 acting as a tripler. As yet another example, the front end could operate at 0.9 to 1.1 GHz, which would correspond to a 3.6 to 4.4 GHz band for the back end, with the frequency multiplier 1325 acting as a quadrupler.

Figure 14:
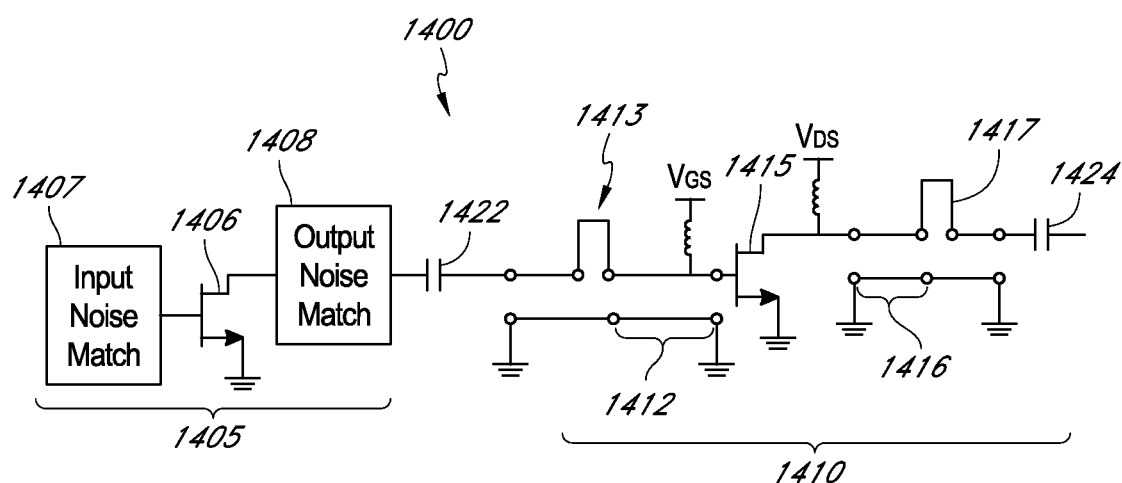
FIG. 14 is a schematic circuit diagram of an embodiment of a low noise frequency doubler for use in a radiometer system.

FIG. 14 is a schematic circuit diagram of an embodiment of a low noise frequency doubler 1400. The front end of the circuit comprises a low-noise amplifier circuit 1405 composed of a transistor 1406, an input noise matching network 1407 and an output noise matching network 1408. The transistor 1406 may comprise a single field-effect transistor (FET), high-electron-mobility transistor (HEMT), pseudomorphic high-electron-mobility transistor (pHEMTs), bipolar junction transistor (BJTs), and/or other type of transistor, as desired or required. The output of the amplifier circuit 1405 feeds into a frequency multiplier circuit 1410. The frequency multiplier circuit 1410 comprises a frequency doubler composed of an input network comprising a second harmonic reflector 1413, spaced away from a single transistor 1415 by an input transmission line 1412. The frequency multiplier circuit 1410 also includes an output network comprised of a fundamental frequency reflector 1417, spaced away from the transistor 1415 by an output transmission line 1416. A single transistor 1415 is positioned between the input module 1412 and the output module 1416. Each of the reflectors 1413, 1417 may be spaced away from the transistor 1415, utilizing the transmission lines 1412 and 1416, for optimal conversion efficiency from the lower frequency to the higher frequency. The bias point may be chosen to enhance the conversion efficiency, such as by biasing the device near pinch off (for example, in a class B type configuration). One or more bypass capacitors 1422, 1424 may be positioned at various locations such as illustrated in FIG. 14 to separate the transistor DC bias voltages from the rest of the microwave circuit.

In some embodiments, matching networks may be created that simultaneously perform optimal noise matching and matching for frequency multiplication. In such embodiments, the separate transistors 1406, 1415 may be replaced with a single transistor that is utilized to perform both the low-noise amplification and frequency multiplication, thereby reducing the overall circuit size. In other embodiments, multiple transistors may be used instead of a single transistor for either transistor 1406 or transistor 1415.

In some embodiments, the system comprises various features that are present as single features (as opposed to multiple features). For example, in one embodiment, the system includes a single ablation catheter with a single antenna, a single energy delivery radiofrequency electrode and a single microwave radiometer. The antenna and radiofrequency electrode may form a single, unitary, or integral, construct at the distal end of the catheter. A single thermocouple (or other means for measuring temperature) may also be included. The system may comprise an impedance transformation network as described herein. Multiple features or components are provided in alternate embodiments.

In some embodiments, the system comprises one or more of the following: means for tissue modulation (for example, an ablation or other type of modulation catheter or delivery device), means for generating energy (for example, a generator or other energy delivery module), means for connecting the means for generating energy to the means for tissue modulation (for example, an interface or input/output connector or other coupling member), means for displaying (for example, a monitor, screen or user interface), means for multiplying or increasing frequency (for example, frequency multipliers, amplifiers), means for receiving energy emissions (for example, an antenna), etc.

In some embodiments, the system comprises various features that are present as single features (as opposed to multiple features). For example, in one embodiment, the system includes a single ablation catheter with a single antenna, a single energy delivery radiofrequency electrode and a single microwave radiometer. The antenna and radiofrequency electrode may form a single, unitary, or integral, construct at the distal end of the catheter. A single thermocouple (or other means for measuring temperature) may also be included. Multiple features or components are provided in alternate embodiments.

In some embodiments, the system comprises one or more of the following: means for tissue modulation (for example, an ablation or other type of modulation catheter or delivery device), means for generating energy (for example, a generator or other energy delivery module), means for connecting the means for generating energy to the means for tissue modulation (for example, an interface or input/output connector or other coupling member), means for displaying (for example, a monitor, screen or user interface), etc.

Any methods described herein may be embodied in, and partially or fully automated via, software code modules executed by one or more processors or other computing devices. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

In addition, embodiments may be implemented as computer-executable instructions stored in one or more tangible computer storage media. As will be appreciated by a person of ordinary skill in the art, such computer-executable instructions stored in tangible computer storage media define specific functions to be performed by computer hardware such as computer processors. In general, in such an implementation, the computer-executable instructions are loaded into memory accessible by at least one computer processor. The at least one computer processor then executes the instructions, causing computer hardware to perform the specific functions defined by the computer-executable instructions. As will be appreciated by a person of ordinary skill in the art, computer execution of computer-executable instructions is equivalent to the performance of the same functions by electronic hardware that includes hardware circuits that are hardwired to perform the specific functions. As such, while embodiments illustrated herein are typically implemented as some combination of computer hardware and computer-executable instructions, the embodiments illustrated herein could also be implemented as one or more electronic circuits hardwired to perform the specific functions illustrated herein.

The various systems, devices and/or related methods disclosed herein can be used to at least partially ablate and/or otherwise ablate, modulate (for example, ablate or stimulate), heat or otherwise thermally treat one or more portions of a subject's anatomy, including without limitation, cardiac tissue (for example, myocardium, atrial tissue, ventricular tissue, valves, etc.), a bodily lumen (for example, vein, artery, airway, esophagus or other digestive tract lumen, urethra and/or other urinary tract vessels or lumens, other lumens, etc.), sphincters, other organs, tumors and/or other growths, nerve tissue and/or any other portion of the anatomy. The selective ablation, modulation and/or other heating of such anatomical locations can be used to treat one or more diseases or conditions, including, for example, atrial fibrillation, mitral valve regurgitation, other cardiac diseases, asthma, chronic obstructive pulmonary disease (COPD), other pulmonary or respiratory diseases, including benign or cancerous lung nodules, hypertension, heart failure, denervation, renal failure, obesity, diabetes, gastroesophageal reflux disease (GERD), other gastroenterological disorders, other nerve-related disease, tumors or other growths, pain and/or any other disease, condition or ailment.

In any of the embodiments disclosed herein, one or more components, including a processor, computer-readable medium or other memory, controllers (for example, dials, switches, knobs, etc.), displays (for example, temperature displays, timers, etc.) and/or the like are incorporated into and/or coupled with (for example, reversibly or irreversibly) one or more modules of the generator, the irrigation system (for example, irrigant pump, reservoir, etc.) and/or any other portion of an ablation or other modulation system.

Although several embodiments and examples are disclosed herein, the present application extends beyond the specifically disclosed embodiments to other alternative embodiments and/or uses of the embodiments and modifications and equivalents thereof. It is also contemplated that various combinations or subcombinations of the specific features and aspects of the embodiments may be made and still fall within the scope of the disclosure. Accordingly, it should be understood that various features and aspects of the disclosed embodiments can be combined with or substituted for one another in order to form varying modes of the disclosed embodiments. Thus, it is intended that the scope of the disclosure should not be limited by the particular disclosed embodiments described above, but should be determined only by a fair reading of the claims that follow.

While the embodiments disclosed herein are susceptible to various modifications, and alternative forms, specific examples thereof have been shown in the drawings and are herein described in detail. It should be understood, however, that the disclosure is not to be limited to the particular forms or methods disclosed, but, to the contrary, the disclosure covers all modifications, equivalents, and alternatives falling within the spirit and scope of the various embodiments described and the appended claims. The headings used herein are merely provided to enhance readability and are not intended to limit the scope of the embodiments disclosed in a particular section to the features or elements disclosed in that section. The features or elements from one embodiment of the disclosure can be employed by other embodiments of the disclosure. For example, features described in one figure may be used in conjunction with embodiments illustrated in other figures. Any methods disclosed herein need not be performed in the order recited. The methods disclosed herein include certain actions taken by a practitioner; however, they can also include any third-party instruction of those actions, either expressly or by implication. For example, actions such as "advancing a catheter" or "delivering energy to an ablation member" include "instructing advancing a catheter" or "instructing delivering energy to an ablation member," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 20 mm" includes "20 mm." Terms or phrases preceded by a term such as "substantially" include the recited term or phrase.

What is claimed is:

1. A system for facilitating determination of quality of contact between an energy delivery device and at least one area of tissue prior to and during energy delivery, the system comprising:
    a radiofrequency energy generator;
    a radiofrequency energy delivery device comprising a radiofrequency electrode configured to deliver ablative energy provided by the radiofrequency energy generator;
    at least one clock;
    a radiometer;
    a processor configured to:
        extract variability information from a signal received from the radiometer, the variability information including a variability index based on a moving average of the signal received from the radiometer and a set of raw output signal data received from the radiometer;
        determine a level of tissue contact between a distal tip of the energy delivery device and tissue to be ablated based, at least in part, upon the variability information;
        generate an output indicative of the level of tissue contact; and
        contemporaneously display the output indicative of the level of tissue contact and the variability information on a user interface; and
    a reflectometer, the reflectometer being configured to:
        determine a reflection coefficient in the at least one area of tissue, the reflection coefficient being further indicative of the level of tissue contact between the distal tip of the energy delivery device and the at least one area of tissue to be ablated; and
        determine whether the at least one area of tissue is one of an area of intact tissue and an area of ablated tissue based on a change in the reflection coefficient;
    an antenna in communication with the radiometer and the reflectometer, the radiometer being configured to continuously switch between the antenna and a reference load to correct for variations in local temperature, the switching being controlled by the at least one clock; and
    the system being further configured to detect and reduce at least one variability reading, the at least one variability reading being caused by one of a respiratory artifact and a cardiac artifact.

2. The system of claim 1, wherein the level of tissue contact is determined based upon a comparison to at least one threshold.

3. The system of claim 2, wherein the at least one threshold comprises a piecewise linear threshold.

4. The system of claim 2, wherein the at least one threshold is configured to be automatically adjusted based on historical variability information data.

5. The system of claim 1, wherein the level of tissue contact is a qualitative assessment selected from one of: poor contact, medium contact, good contact, and excellent contact.

6. The system of claim 1, further including a diplexer having:
    a band pass filter configured to allow signals in a frequency band of the radiometer to pass through to the radiometer; and
    a band stop filter configured to reject signals in a frequency band of the radiometer.

7. The system of claim 1, further including a reflectometer circuit having:
    a voltage-controlled oscillator;
    a directional coupler configured to sample a microwave signal and discriminate between forward-traveling power and reverse-traveling power; and
    a magnitude detector in communication with the directional coupler.

8. The system of claim 7, wherein the reflectometer circuit further includes a switch configured to toggle between the reference load and the antenna of the energy delivery device.

9. A system for facilitating determination of quality of contact between an energy delivery member and at least one area of tissue prior to and during energy delivery, the system comprising:
    a processor configured to:
        receive a first output signal from a radiometer and a second output signal from a reflectometer, the radiometer and the reflectometer each being carried by an energy delivery member;
        extract variability information, the variability information including a variability index;
        determine a level of tissue contact between the energy delivery member and tissue based, at least in part, upon the extracted variability information and upon a measured reflection coefficient in the at least one area of tissue;

determine whether the at least one area of tissue is one of an area of intact tissue and an area of ablated tissue based on a change in the reflection coefficient;

contemporaneously display the output signal and the level of tissue contact on a user interface;

continuously switch the radiometer between an antenna and a reference load to correct for variations in local temperature, the switching being controlled by at least one clock; and the system being further configured to detect and reduce at least one variability reading, the at least one variability reading being caused by one of a respiratory artifact and a cardiac artifact.

10. The system of claim 9, wherein the level of tissue contact is determined, at least in part, by subtracting a moving average of the first output signal from a set of raw output signal data received from the radiometer.

11. The system of claim 9, wherein the processor is further configured to cause an indicator of the level of tissue contact to be displayed on a display.

12. The system of claim 11, wherein the indicator comprises a color.

13. The system of claim 11, wherein the indicator comprises textual information indicative of the level of tissue contact.

14. The system of claim 9, wherein the level of tissue contact is determined based upon a comparison to at least one threshold.

15. The system of claim 14, wherein the at least one threshold is configured to be automatically adjusted based on historical variability information data.

16. A method of determining contact between an energy delivery device and at least one area of tissue prior to and during energy delivery, the method comprising:

receiving a first output signal from a radiometer and a second output signal from a reflectometer;

extracting variability information based on a moving average of the first output signal and a set of raw output signal data received from the radiometer;

causing an output indicative of the variability information to be displayed on a display;

determining a level of tissue contact based, at least in part, on the variability information and upon a measured reflection coefficient in the at least one area of tissue;

determining whether the at least one area of tissue is one of an area of intact tissue and an area of ablated tissue based on a change in the reflection coefficient;

continuously switching the radiometer between an antenna and a reference load to correct for variations in local temperature, the switching being controlled by at least one clock;

filtering at least one variability reading, the at least one variability reading being caused by one of a respiratory artifact and a cardiac artifact; and contemporaneously causing the level of tissue contact to be displayed on the display.

17. The method of claim 16, wherein the variability information comprises a variability index determined by subtracting the moving average from the set of raw output signal data of the radiometer.

18. The method of claim 17, wherein the moving average comprises a 5-point-moving average.

* * * * *